(12) United States Patent
Watanabe et al.

(10) Patent No.: US 10,763,440 B2
(45) Date of Patent: Sep. 1, 2020

(54) ORGANIC ELECTROLUMINESCENT ELEMENT, AND LIGHT EMITTING DEVICE, DISPLAY DEVICE AND LIGHTING DEVICE EACH USING ORGANIC ELECTROLUMINESCENT ELEMENT

(71) Applicant: UDC Ireland Limited, Dublin (IE)

(72) Inventors: Kousuke Watanabe, Kanagawa (JP); Hiroaki Tsuyama, Kanagawa (JP); Yuichiro Itai, Kanagawa (JP)

(73) Assignee: UDC IRELAND LIMITED, Dublin (IE)

( * ) Notice: Subject to any disclaimer, the term of this patent is extended or adjusted under 35 U.S.C. 154(b) by 1030 days.

(21) Appl. No.: 14/351,156

(22) PCT Filed: Nov. 21, 2012

(86) PCT No.: PCT/JP2012/080132
§ 371 (c)(1),
(2) Date: Jun. 23, 2014

(87) PCT Pub. No.: WO2013/077345
PCT Pub. Date: May 30, 2013

(65) Prior Publication Data
US 2014/0306206 A1      Oct. 16, 2014

(30) Foreign Application Priority Data
Nov. 24, 2011    (JP) ................................. 2011-255990

(51) Int. Cl.
*H01L 51/00* (2006.01)
*C09K 11/06* (2006.01)
(Continued)

(52) U.S. Cl.
CPC ........ *H01L 51/0067* (2013.01); *C07D 209/86* (2013.01); *C07D 235/06* (2013.01);
(Continued)

(58) Field of Classification Search
CPC ............. H01L 51/0067; H01L 51/0071; H01L 51/5088; H01L 51/5056; H01L 51/5072;
(Continued)

(56) References Cited

U.S. PATENT DOCUMENTS

| 2006/0182992 | A1* | 8/2006 | Nii | ........................ | C07C 251/24 428/690 |
| 2009/0309488 | A1* | 12/2009 | Kato | .................... | C07D 487/04 313/504 |
| 2012/0080670 | A1* | 4/2012 | Park | .................... | C07D 209/82 257/40 |

FOREIGN PATENT DOCUMENTS

| JP | 2005310733 | 11/2005 |
| WO | 2009148015 | 12/2009 |

(Continued)

OTHER PUBLICATIONS

Kato et al. (machine translation of WO 2009148015 (Dec. 10, 2009)).*

(Continued)

*Primary Examiner* — Robert H Havlin
(74) *Attorney, Agent, or Firm* — Riverside Law LLP

(57) ABSTRACT

An organic electroluminescent element containing a light emitting material represented by the following general formula (1) and a host material represented by the general formula (H-1) in a light emitting layer. The organic electroluminescent element has low driving voltage, high luminous efficiency, and excellent durability. L represents O, $NR^{C0}$, or $CR^{C1}R^{C2}$; $R^{C0}$ to $R^{C2}$ each represents a hydrogen atom or a substituent; $R^{C3}$ to $R^{C6}$ each represents a substituent; $n^{C3}$ and $n^{C6}$ each represents an integer of 0 to 3; $n^{C4}$ and $n^{C5}$ each represents an integer of 0 to 4; $R^{H111}$ to $R^{H118}$ each represents a hydrogen atom or a substituent; X represents any one of O, S, $NR^{H119}$, $CR^{H120}R^{H121}$, and $SiR^{H122}R^{H123}$, and $R^{H119}$ to $R^{H123}$ each represents a substituent; the ring A represents a benzene ring; and the ring B represents a 5- or 6-membered ring.

General Formula (1)

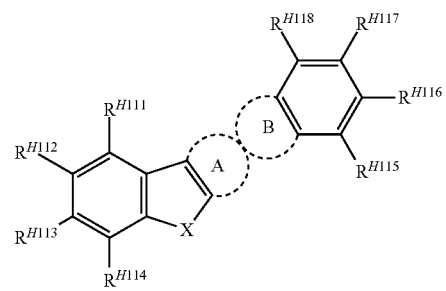

General Formula (H-1)

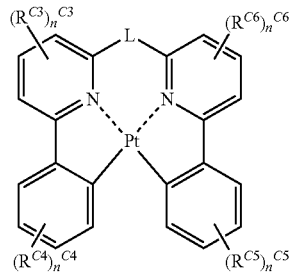

10 Claims, 1 Drawing Sheet

(51) Int. Cl.
  H05B 33/14   (2006.01)
  C07D 471/04  (2006.01)
  C07D 209/86  (2006.01)
  C07D 307/91  (2006.01)
  C07D 487/04  (2006.01)
  C07D 495/04  (2006.01)
  C07D 491/048 (2006.01)
  C07D 409/10  (2006.01)
  C07D 519/00  (2006.01)
  C07D 235/06  (2006.01)
  C07D 333/76  (2006.01)
  C07D 401/14  (2006.01)
  H01L 51/50   (2006.01)

(52) U.S. Cl.
  CPC ........ *C07D 307/91* (2013.01); *C07D 333/76* (2013.01); *C07D 401/14* (2013.01); *C07D 409/10* (2013.01); *C07D 471/04* (2013.01); *C07D 487/04* (2013.01); *C07D 491/048* (2013.01); *C07D 495/04* (2013.01); *C07D 519/00* (2013.01); *C09K 11/06* (2013.01); *H01L 51/0071* (2013.01); *H01L 51/0087* (2013.01); *H01L 51/5056* (2013.01); *H01L 51/5072* (2013.01); *H01L 51/5088* (2013.01); *H01L 51/5092* (2013.01); *H05B 33/14* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *C09K 2211/1088* (2013.01); *C09K 2211/1092* (2013.01); *C09K 2211/185* (2013.01); *H01L 51/0059* (2013.01); *H01L 51/0072* (2013.01); *H01L 51/5016* (2013.01)

(58) Field of Classification Search
  CPC ............ H01L 51/5092; H01L 51/0087; H01L 51/5016; H01L 51/0072; H01L 51/0059; C07D 401/14; C07D 409/10; C07D 519/00; C07D 487/04; C07D 491/048; C07D 235/06; C07D 209/86; C07D 333/76; C07D 307/91; C07D 471/04; C07D 495/04; H05B 33/14; C09K 11/06; C09K 2211/1007; C09K 2211/1088; C09K 2211/1011; C09K 2211/1044; C09K 2211/1014; C09K 2211/185; C09K 2211/1029; C09K 2211/1092
  See application file for complete search history.

(56) References Cited

FOREIGN PATENT DOCUMENTS

| WO | 2009148062 | 12/2009 |
| WO | 2010131855 | 11/2010 |
| WO | 2011057701 | 5/2011 |
| WO | 2012163471 | 6/2012 |
| WO | 2012136295 | 10/2012 |

OTHER PUBLICATIONS

International Preliminary Report on Patentability for International Patent Application No. PCT/JP2012/080132, dated Jun. 5, 2014, 7 pages.
International Search Report for International Patent Application No. PCT/JP2012/080132, dated Feb. 26, 2013, 4 pages.
International Publication for International Patent Application No. PCT/JP2012/080132, dated May 30, 2013, 77 pages.
Written Opinion for International Patent Application No. PCT/JP2012/080132, dated Feb. 26, 2013, 5 pages.

* cited by examiner

ORGANIC ELECTROLUMINESCENT ELEMENT, AND LIGHT EMITTING DEVICE, DISPLAY DEVICE AND LIGHTING DEVICE EACH USING ORGANIC ELECTROLUMINESCENT ELEMENT

CROSS-REFERENCE TO RELATED APPLICATIONS

This application is a national stage entry of International Patent Application No. PCT/JP2012/080132, filed 21 Nov. 2012, which in turn claims priority to, and the benefit of, Japanese Patent Application No. 2011-255990, filed 24 Nov. 2011, all of which are incorporated herein by reference in their entireties.

TECHNICAL FIELD

The present invention relates to an organic electroluminescent element. The present invention further relates to a light emitting device, a display device, and an illumination device each using the organic electroluminescent element.

BACKGROUND ART

Since organic electroluminescent elements (which may hereinafter also be referred to as "elements" or "organic EL elements") are capable of high-luminance light emitting with driving at a low voltage, they have been actively researched and developed. The organic electroluminescent elements have organic layers between a pair of electrodes, and utilize, for light emitting, energy of the exciton generated as a result of recombination of electrons injected from a cathode and holes injected from an anode in the organic layer. Since the organic electroluminescent elements are capable of being provided as an element having various light emitting wavelengths, have a high response speed, and are relatively thin and light-weight, it is expected that the element can be employed in a wide range of applications. Above all, it is important to develop an organic electroluminescent element having green phosphorescent light emission, low driving voltage, high luminous efficiency, and high durability in applications with full-color displays, and the like, and the outcomes of various research and development studies up to now have been reported.

PTL 1 describes an organic electroluminescent element, in which a platinum complex having a specific structure, or the like is used as a light emitting material of a light emitting layer, and also describes that a phosphorescent light emitting element having good color purity and element durability can be provided. PTL 1 describes fused aromatic carbocyclic compounds, non-complex aromatic nitrogen-containing heterocyclic compounds, and the like as an example of a host material of a light emitting layer, but discloses only Examples, in which carbazole-based compounds or beryllium complexes are used.

On the other hand, PTL 2 describes an organic electroluminescent element, in which a polycyclic fused-ring compound with 5 or more rings is used as a host material of a light emitting layer, with the use of a platinum complex having a specific structure, which is a red light emitting material, as a light emitting material of a light emitting layer. However, in PTL 2, only a material having a structure exhibiting red light emission is employed for the platinum complex, and accordingly, the performance of an organic electroluminescent element obtained in the case of using a platinum complex having a structure exhibiting green light emission is unclear.

PTL 3 describes an organic electroluminescent element, in which a polycyclic fused-ring compound with 5 or more rings is used as a host material of a light emitting layer and an iridium complex having a specific structure is used as a light emitting material of the light emitting layer, and also describes that an element having excellent luminous efficiency and durability can be provided. However, PTL 3 does not describe Examples, in which a platinum complex is used as a light emitting material.

PTL 4 describes an organic electroluminescent element, in which a polycyclic fused-ring compound with 5 or more rings is used as a host material of a light emitting layer and an iridium complex having a specific structure is used as a light emitting material of the light emitting layer, and also describes that an element excellent in terms of luminous efficiency, pixel defects, and service life can be provided. However, PTL 4 describes various platinum complexes as a light emitting material and does not describe Examples, in which a platinum complex is used.

CITATION LIST

Patent Literature

[PTL 1] JP-A-2005-310733
[PTL 2] WO2011/057701
[PTL 3] JP-A-2011-091355
[PTL 4] WO2009/148062

SUMMARY OF INVENTION

Technical Problem

The present inventors have investigated the organic electroluminescent elements described in PTLs 1 to 4, and as a result, it could be seen that complaints from the viewpoint of lower power and higher efficiency remain, and accordingly, there is a demand of additional improvement in durability. Further, PTLs 1 to 4 neither mention nor describe to suggest a combined use of a platinum complex having a structure used for green light emission with a light emitting material in the case of using a polycyclic fused-ring compound with 5 or more rings as a host material of a light emitting layer, or the characteristics of an element in the case of such a combined use.

The present invention aims to solve the aforementioned problems. That is, to solve the aforementioned problems, the present invention is made to provide an organic electroluminescent element having low driving voltage, high luminous efficiency, and excellent durability.

Solution to Problem

The present inventors have conducted extensive investigations to solve the aforementioned problems, and as a result, they have found that an organic electroluminescent element having low driving voltage, high luminous efficiency, and excellent durability can be provided by using a polycyclic fused-ring compound having a specific structure as a host material to give a light emitting layer, with the use of a platinum complex having a specific structure as a light emitting material.

The present invention which is specific means for solving the aforementioned problems is as follows.

[1] An organic electroluminescent element including a substrate, a pair of electrodes including an anode and a cathode, disposed on the substrate, and at least one organic layer including a light emitting layer, disposed between the electrodes, in which the light emitting layer contains at least one kind of light emitting material represented by the following general formula (1) and at least one kind of host material represented by the following general formula (H-1).

General Formula (1)

[Chem. 1]

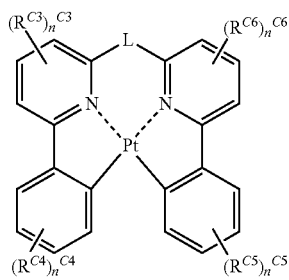

(In the general formula (1), L represents O, $NR^{C0}$, or $CR^{C1}R^{C2}$, and $R^{C0}$ to $R^{C2}$ each independently represent a hydrogen atom or a substituent. $R^{C3}$ to $R^{C6}$ each independently represent a substituent. $n^{C3}$ and $n^{C6}$ each independently represent an integer of 0 to 3, and $n^{C4}$ and $n^{C5}$ each independently represent an integer of 0 to 4. In the case where $n^{C3}$ to $n^{C6}$ are 2 or more, a plurality of $R^{C3}$s to $R^{C6}$s may be respectively the same as or different from each other and may be connected with each other to form a ring.)

General Formula (H-1)

[Chem. 2]

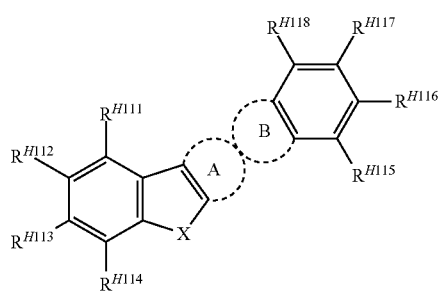

(In the general formula (H-1), $R^{H111}$ to $R^{H118}$ each independently represent a hydrogen atom or a substituent, X represents any one of O, S, $NR^{H119}$, $CR^{H120}R^{H121}$, $SiR^{H122}R^{H123}$, and $R^{H119}$ to $R^{H123}$ each independently represent a substituent. The ring A represents a benzene ring and the ring B represents a 5- or 6-membered ring.)

[2] In the organic electroluminescent element as described in [1], the light emitting material represented by the general formula (1) is preferably a light emitting material represented by the following general formula (11).

[Chem. 3]

General Formula (11)

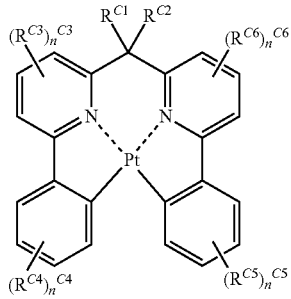

(In the general formula (11), $R^{C1}$ and $R^{C2}$ each independently represent a hydrogen atom or a substituent, and $R^{C3}$ to $R^{C6}$ each independently represent a substituent. $n^{C3}$ and $n^{C6}$ each represent an integer of 0 to 3, and $n^{C4}$ and $n^{C5}$ each represent an integer of 0 to 4. In the case where $n^{C3}$ to $n^{C6}$ are 2 or more, a plurality of $R^{C3}$s to $R^{C6}$s may be the same as or different from each other and may be connected with each other to form a ring.)

[3] In the organic electroluminescent element as described in [1] or [2], the host material represented by the general formula (H-1) is preferably represented by any one of the following general formulae (H-2), (H-3), (H-4), and (H-5).

[Chem. 4]

General Formula (H-2)

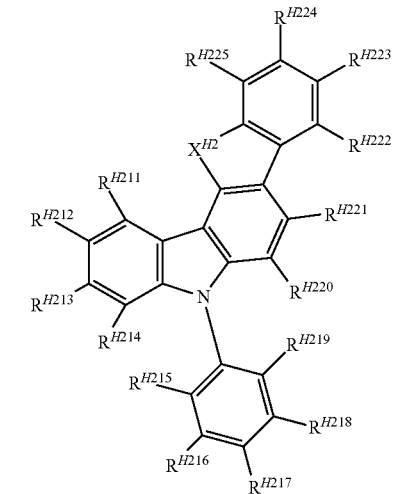

(In the general formula (H-2), $R^{H211}$ to $R^{H225}$ each independently represent a hydrogen atom or a substituent, and $X^{H2}$ represents either of O and S.)

General Formula (H-3)

[Chem. 5]

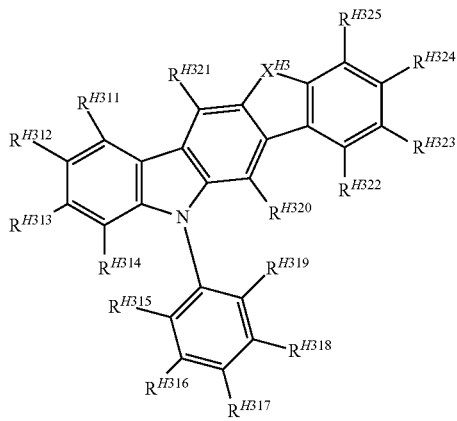

(In the general formula (H-3), $R^{H311}$ to $R^{H325}$ each independently represent a hydrogen atom or a substituent, and $X^{H3}$ represents either of O and S.)

[Chem. 6]

General Formula (H-4)

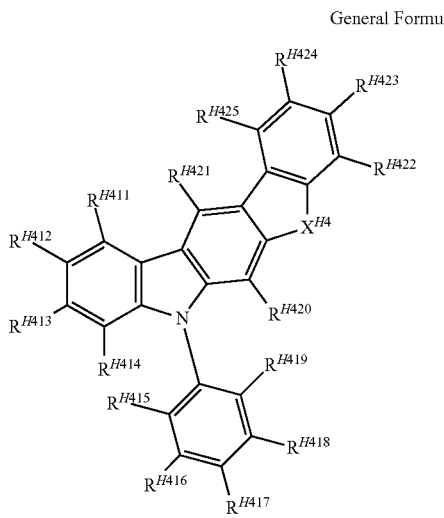

(In the general formula (H-4), $R^{H411}$ to $R^{H425}$ each independently represent a hydrogen atom or a substituent, $X^{H4}$ represents any one of O, S, $NR^{H426}$, $CR^{H427}R^{H428}$, and $SiR^{H429}R^{H430}$, and $R^{H426}$ to $R^{H430}$ each independently represent a hydrogen atom or a substituent.)

[Chem. 7]

General Formula (H-5)

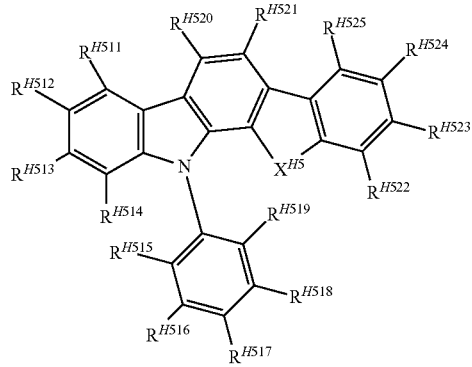

(In the general formula (H-5), $R^{H511}$ to $R^{H525}$ each independently represent a hydrogen atom or a substituent, $X^{H5}$ represents any one of O, S, $NR^{H526}$, $CR^{H527}R^{H528}$, and $SiR^{H529}R^{H530}$, and $R^{H526}$ to $R^{H530}$ each independently represent a hydrogen atom or a substituent.)

[4] In the organic electroluminescent element as described in [3], the host material represented by the general formula (H-1) is preferably represented by the general formula (H-2) or (H-5).

[5] In the organic electroluminescent element as described in [3] or [4], the host material represented by the general formula (H-1) is preferably represented by the general formula (H-2).

[6] A light emitting device using the organic electroluminescent element as described in any one of [1] to [5].

[7] A display device using the organic electroluminescent element as described in any one of [1] to [5].

[8] An illumination device using the organic electroluminescent element as described in any one of [1] to [5].

Advantageous Effects of Invention

The organic electroluminescent element of the present invention has low driving voltage, high luminous efficiency, and excellent durability. In addition, the light emitting device, the display device, and the illumination device of the present invention have advantageous effects in that the power consumption is low and the durability is excellent.

DESCRIPTION OF EMBODIMENTS

Figure 1:
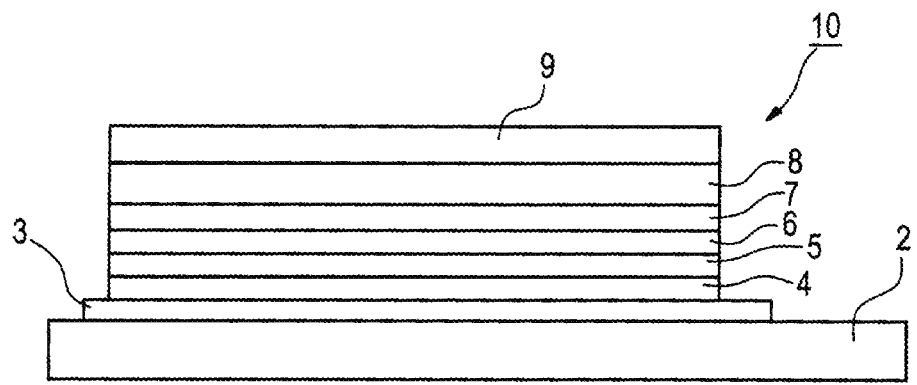
FIG. 1 is a schematic view showing one example of a configuration of an organic electroluminescent element according to the present invention.

Hereinafter, the disclosure of the present invention will be described in detail. The description of the requirements of the configuration as described below is based on representative embodiments and specific examples of the present invention, but the present invention is not limited to these embodiments and specific examples. Incidentally, in the present specification, the range expressed with "to" means a range including the numerical values before and after "to" as the lower limit and the upper limit, respectively.

In the present invention, the hydrogen atom which is used without particular distinction at each occurrence in the description of the respective general formulae also includes isotopes (a deuterium atom and the like), and the atoms additionally constituting the substituent are also intended to include isotopes of the atoms.

[Organic Electroluminescent Element]

The organic electroluminescent element of the present invention includes a substrate, a pair of electrodes including an anode and a cathode, disposed on the substrate, and at least one organic layer including a light emitting layer, disposed between the electrodes, in which the light emitting layer contains at least one kind of light emitting material represented by the following general formula (1) and at least one kind of host material represented by the following general formula (H-1).

Hereinafter, the structure of the light emitting material represented by the general formula (1) (hereinafter also referred to as the compound represented by the general formula (1)), the structure of the host emitting material represented by the general formula (H-1) (hereinafter also referred to as the compound represented by the general formula (H-1)), and other configurations of the organic electroluminescent element of the present invention will be described in detail.

<Light Emitting Material Represented by General Formula (1)>

In the organic electroluminescent element of the present invention, the light emitting layer contains at least one kind of light emitting material represented by the following general formula (1).

[Chem. 8]

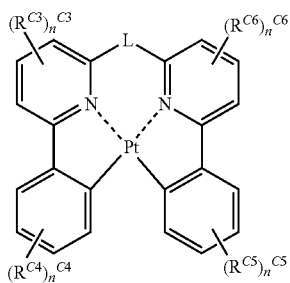

General Formula (1)

(In the general formula (1), L represents O, $NR^{C0}$, or $CR^{C1}R^{C2}$, and $R^{C0}$ to $R^{C2}$ each independently represent a hydrogen atom or a substituent. $R^{C3}$ to $R^{C6}$ each independently represent a substituent. $n^{C3}$ and $n^{C6}$ each independently represent an integer of 0 to 3, and $n^{C4}$ and $n^{C5}$ each independently represent an integer of 0 to 4. In the case where $n^{C3}$ to $n^{C6}$ are 2 or more, a plurality of $R^{C3}$s to $R^{C6}$s may be respectively the same as or different from each other and may be connected with each other to form a ring.)

In the general formula (1), L represents O, $NR^{C0}$, or $CR^{C1}R^{C2}$, and $R^{C0}$ to $R^{C2}$ each independently represent a hydrogen atom or a substituent. Examples of the substituents represented by $R^{C1}$ and $R^{C2}$ include the following Substituent Group A, and examples of the substituent represented by $R^{C0}$ include the following Substituent Group A.

(Substituent Group A)

An alkyl group (preferably having 1 to 30 carbon atoms, more preferably having 1 to 20 carbon atoms, and particularly preferably having 1 to 10 carbon atoms; for example, methyl, ethyl, isopropyl, tert-butyl, n-octyl, n-decyl, n-hexadecyl, cyclopropyl, cyclopentyl, and cyclohexyl), an alkenyl group (preferably having 2 to 30 carbon atoms, more preferably having 2 to 20 carbon atoms, and particularly preferably having 2 to 10 carbon atoms, for example, vinyl, allyl, 2-butenyl, and 3-pentenyl), an alkynyl group (preferably having 2 to 30 carbon atoms, more preferably having 2 to 20 carbon atoms, and particularly preferably having 2 to 10 carbon atoms, for example, propargyl and 3-pentynyl), an aryl group (preferably having 6 to 30 carbon atoms, more preferably having 6 to 20 carbon atoms, and particularly preferably having 6 to 12 carbon atoms, for example, phenyl, p-methylphenyl, naphthyl, and anthranyl), an amino group (preferably having 0 to 30 carbon atoms, more preferably having 0 to 20 carbon atoms, and particularly preferably having 0 to 10 carbon atoms; for example, amino, methylamino, dimethylamino, diethylamino, dibenzylamino, diphenylamino, and ditolylamino), an alkoxy group (preferably having 1 to 30 carbon atoms, more preferably having 1 to 20 carbon atoms, and particularly preferably having 1 to 10 carbon atoms; for example, methoxy, ethoxy, butoxy, and 2-ethylhexyloxy), an aryloxy group (preferably having 6 to 30 carbon atoms, more preferably having 6 to 20 carbon atoms, and particularly preferably having 6 to 12 carbon atoms; for example, phenyloxy, 1-naphthyloxy, and 2-naphthyloxy), a heterocyclic oxy group (preferably having 1 to 30 carbon atoms, more preferably having 1 to 20 carbon atoms, and particularly preferably having 1 to 12 carbon atoms; for example, pyridyloxy, pyrazyloxy, pyrimidyloxy, and quinolyloxy), an acyl group (preferably having 2 to 30 carbon atoms, more preferably having 2 to 20 carbon atoms, and particularly preferably having 2 to 12 carbon atoms; for example, acetyl, benzoyl, formyl, and pivaloyl), an alkoxycarbonyl group (preferably having 2 to 30 carbon atoms, more preferably having 2 to 20 carbon atoms, and particularly preferably having 2 to 12 carbon atoms; for example, methoxycarbonyl and ethoxycarbonyl), an aryloxycarbonyl group (preferably having 7 to 30 carbon atoms, more preferably having 7 to 20 carbon atoms, and particularly preferably having 7 to 12 carbon atoms; for example, phenyloxycarbonyl), an acyloxy group (preferably having 2 to 30 carbon atoms, more preferably having 2 to 20 carbon atoms, and particularly preferably having 2 to 10 carbon atoms; for example, acetoxy and benzoyloxy), an acylamino group (preferably having 2 to 30 carbon atoms, more preferably having 2 to 20 carbon atoms, and particularly preferably having 2 to 10 carbon atoms; for example, acetylamino and benzoylamino), an alkoxycarbonylamino group (preferably having 2 to 30 carbon atoms, more preferably having 2 to 20 carbon atoms, and particularly preferably having 2 to 12 carbon atoms; for example, methoxycarbonylamino), an aryloxycarbonylamino group (preferably having 7 to 30 carbon atoms, more preferably having 7 to 20 carbon atoms, and particularly preferably having 7 to 12 carbon atoms; for example, phenyloxycarbonylamino), a sulfonylamino group (preferably having 1 to 30 carbon atoms, more preferably having 1 to 20 carbon atoms, and particularly preferably having 1 to 12 carbon atoms; for example, methanesulfonylamino and benzenesulfonylamino), a sulfamoyl group (preferably having 0 to 30 carbon atoms, more preferably having 0 to 20 carbon atoms, and particularly preferably having 0 to 12 carbon atoms; for example, sulfamoyl, methylsulfamoyl, dimethylsulfamoyl, and phenylsulfamoyl), a carbamoyl group (preferably having 1 to 30 carbon atoms, more preferably having 1 to 20 carbon atoms, and particularly preferably having 1 to 12 carbon atoms; for example, carbamoyl, methylcarbamoyl, diethylcarbamoyl, and phenylcarbamoyl), an alkylthio group (preferably having 1 to 30 carbon atoms, more preferably having 1 to 20 carbon atoms, and particularly preferably having 1 to 12 carbon atoms; for example, methylthio and ethylthio), an arylthio group (preferably having 6 to 30 carbon atoms, more preferably having 6 to 20 carbon atoms, and particularly preferably having 6 to 12 carbon atoms; for example, phenylthio), a heterocyclic thio group (preferably having 1 to 30 carbon atoms, more preferably having 1 to 20 carbon atoms, and particularly preferably having 1 to 12 carbon atoms; for example, pyridylthio, 2-benzoimizolylthio, 2-benzoxazolylthio, and 2-benzothiazolylthio), a sulfonyl group (preferably having 1 to 30 carbon atoms, more preferably having 1 to 20 carbon atoms, and particularly preferably having 1 to 12 carbon atoms; for example, mesyl and tosyl), a sulfinyl group (preferably having 1 to 30 carbon atoms, more preferably having 1 to 20 carbon atoms, and particularly preferably having 1 to 12 carbon atoms; for example, methanesulfinyl and benzenesulfinyl), a ureido group (preferably having 1 to 30 carbon atoms, more preferably having 1 to 20 carbon atoms, and particularly preferably having 1 to 12 carbon atoms; for example, ureido, methylureido, and phenylureido), a phosphoramide group (preferably having 1 to 30 carbon atoms, more preferably having 1 to 20 carbon atoms, and particularly preferably having 1 to 12 carbon atoms; for example, diethyl phosphoramide and phenyl phosphoramide), a hydroxyl group, a mercapto group, a halogen atom (for example, a fluorine atom, a chlorine atom, a bromine atom, and an iodine atom), a cyano group, a sulfo group, a carboxyl group, a nitro group, a hydroxamic group, a sulfino group, a hydrazino group, an imino group, a heterocyclic group (inclusive of an aromatic heterocyclic group, which preferably has 1 to 30 carbon atoms, and more preferably 1 to 12 carbon atoms and in which examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzoimidazolyl, benzothiazolyl, a carbazolyl group, an azepinyl group, and a silolyl group), a silyl group (preferably having 3 to 40 carbon atoms, more preferably having 3 to 30 carbon atoms, and particularly preferably having 3 to 24 carbon atoms; for example, trimethylsilyl and triphenylsilyl), a silyloxy group (preferably having 3 to 40 carbon atoms, more preferably having 3 to 30 carbon atoms, and particularly preferably having 3 to 24 carbon atoms; for example, trimethylsilyloxy and triphenylsilyloxy), and a phosphoryl group (for example, a diphenylphosphoryl group and a dimethylphosphoryl group).

(Substituent Group B)

An alkyl group (preferably having 1 to 30 carbon atoms, more preferably having 1 to 20 carbon atoms, and particularly preferably having 1 to 10 carbon atoms; for example, methyl, ethyl, isopropyl, tert-butyl, n-octyl, n-decyl, n-hexadecyl, cyclopropyl, cyclopentyl, and cyclohexyl), an alkenyl group (preferably having 2 to 30 carbon atoms, more preferably having 2 to 20 carbon atoms, and particularly preferably having 2 to 10 carbon atoms; for example, vinyl, allyl, 2-butenyl, and 3-pentenyl), an alkynyl group (preferably having 2 to 30 carbon atoms, more preferably having 2 to 20 carbon atoms, and particularly preferably having 2 to 10 carbon atoms; for example, propargyl and 3-pentynyl), an aryl group (preferably having 6 to 30 carbon atoms, more preferably having 6 to 20 carbon atoms, and particularly preferably having 6 to 12 carbon atoms; for example, phenyl, p-methylphenyl, naphthyl, and anthranyl), a cyano group, and a heterocyclic group (inclusive of an aromatic heterocyclic group, which preferably has 1 to 30 carbon atoms, and more preferably 1 to 12 carbon atoms and in which examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzoimidazolyl, benzothiazolyl, a carbazolyl group, an azepinyl group, and a silolyl group).

In the present invention, the "number of carbon atoms" of the substituents such as an alkyl group includes a case where the substituents such as an alkyl group may be substituted with another substituent and is used to mean the number including the number of carbon atoms of the other substituents.

$R^{C0}$ is preferably the Substituent Group B among a hydrogen atom or the Substituent Group B, more preferably an alkyl group or an aryl group, particularly preferably an aryl group, and more particularly preferably a phenyl group.

$R^{C0}$ may have an additional substituent, examples of the additional substituent include the substituents represented by the Substituent Group A, and above all, an alkyl group and an aryl group are preferred.

$R^{C1}$ and $R^{C2}$ are each preferably the Substituent Group A among a hydrogen atom or the Substituent Group A, more preferably an alkyl group or an aryl group, and still more preferably an alkyl group.

$R^{C1}$ and $R^{C2}$ may have an additional substituent, examples of the additional substituent include the substituents represented by the Substituent Group A, and above all, an alkyl group is preferred.

Furthermore, $R^{C1}$ and $R^{C2}$ may be bonded to each other to form a ring.

L is preferably $NR^{C0}$ or $CR^{C1}R^{C2}$ from the viewpoint of the stability of a complex and the luminous quantum yield, and more preferably $CR^{C1}R^{C2}$. That is, the compound represented by the general formula (1) is more preferably represented by the following general formula (11).

[Chem. 9]

General Formula (11)

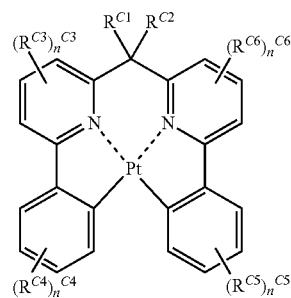

In the general formula (11), $R^{C1}$ and $R^{C2}$ each independently represent a hydrogen atom or a substituent, and $R^{C3}$ to $R^{C6}$ each independently represent a substituent. $n^{C3}$ and $n^{C6}$ each represent an integer of 0 to 3, and $n^{C4}$ and $n^{C5}$ each represent an integer of 0 to 4. In the case where $n^{C3}$ to $n^{C6}$ are 2 or more, a plurality of $R^{C3}$s to $R^{C6}$s may be the same as or different from each other and may be connected with each other to form a ring.

The preferred ranges of $R^{C1}$ to $R^{C6}$ and $n^{C3}$ to $n^{C6}$ in the general formula (11) are the same as the preferred ranges of $R^{C1}$ to $R^{C6}$ and $n^{C3}$ to $n^{C6}$ in the general formula (1).

In the general formula (1), $R^{C1}$ and $R^{C2}$ are more preferably a methyl group, an ethyl group, a propyl group, an isobutyl group, a benzyl group, or a phenyl group, among an alkyl group, or an aryl group.

In the general formula (1), L is more preferably a dimethylmethylene group, a diethylmethylene group, a diisobutylmethylene group, a dibenzylmethylene group, an ethylmethylmethylene group, a methylpropyl methylene group, an isobutyl methylmethylene group, a diphenylmethylene group, a methylphenylmethylene group, a cyclohexanediyl group, a cyclopentanediyl group, a fluorenediyl group, or a fluoromethylmethylene group, and particularly preferably a dimethylmethylene group or a diphenylmethylene group (in which the phenyl groups are preferably bonded to each other to form a fluorene ring).

In the general formula (1), $R^{C3}$ to $R^{C6}$ each independently represent a substituent. Examples of the substituent represented by $R^{C3}$ to $R^{C6}$ include the Substituent Group A, preferably an alkyl group (more preferably an alkyl group having 1 to 3 carbon atoms, and particularly preferably a methyl group and a t-butyl group), an alkenyl group, an aryl group (more preferably a phenyl group, a 2-methylphenyl group, a 2,6-dimethylxylyl group, and a 3,5-dimethylxylyl group), an amino group, an alkoxy group, an aryloxy group, a halogen atom (more preferably a fluorine atom), a halogenated alkyl group (preferably a trifluoromethyl group and a perfluoroalkyl group), or a cyano group, more preferably an alkyl group, an aryl group, or a cyano group, and particularly preferably an aryl group.

$R^{C3}$ to $R^{C6}$ may have an additional substituent, and examples of the additional substituent include the substituents represented by the Substituent Group A. Above all, as the additional substituent on an alkyl group or an aryl group, an alkyl group, an aryl group, a fluorine atom, a cyano group, an arylthio group, and an aryloxy group are preferred (the additional substituents may be bonded to each other to form a fused ring, for example, $R^{C3}$ to $R^{C6}$ preferably entirely constitute a dibenzothiophenyl group or a dibenzofuranyl group), and as the additional substituent on an amino group, an alkyl group or an aryl group is preferred.

In the case where $n^{C3}$ to $n^{C6}$ are 2 or more, a plurality of $R^{C3}$s to $R^{C6}$s may be the same as or different from each other. In this case, a plurality of $R^{C3}$s to $R^{C6}$s may be bonded to each other to form a ring, and preferably form a benzene ring, a pyrrole ring, a thiophene ring, a furan ring, a cyclopentadiene ring, or a silole ring. In the case of forming a pyrrole ring, a thiophene ring, a furan ring, a cyclopentadiene ring, or a silole ring, the ring is preferably further fused with a benzene ring.

$n^{C3}$ and $n^{C6}$ each represent an integer of 0 to 3, preferably 0 to 2, and more preferably 0.

$n^{C4}$ and $n^{C5}$ each represent an integer of 0 to 4, and preferably 0 to 2.

Here, the general formula (11) may be represented by the following general formula (12). Hereinafter, the preferred range of the general formula (11) will be described, based on the following general formula (12).

[Chem. 10]

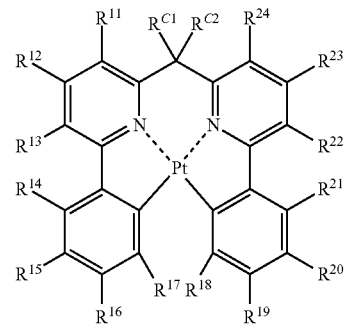

General Formula (12)

In the general formula (12), $R^{C1}$ and $R^{C2}$ have the same definitions as $R^{C1}$ and $R^{C2}$ in the general formula (1), $R^{11}$ to $R^{13}$ each independently represent (3-$n^{C3}$) hydrogen atoms or $n^{C3}$ $R^{C3}$s, $R^{14}$ to $R^{17}$ each independently represent (4-$n^{C4}$) hydrogen atoms or $n^{C4}R^{C4}$s, $R^{18}$ to $R^{21}$ each independently represent (4-$n^{C5}$) hydrogen atoms or $n^{C5}R^{C5}$s and $R^{22}$ to $R^{24}$ each independently represent (3-$n^{C6}$) hydrogen atoms or $n^{C6}R^{C6}$s.

In the general formula (12), $R^{11}$ to $R^{24}$ are each independently preferably a hydrogen atom, an alkyl group, an aryl group, a halogen atom, a halogenated alkyl group, or a cyano group.

Furthermore, the preferred range of each of the substituents represented by $R^{11}$ to $R^{24}$ in the general formula (12) is the same as the preferred range of each of the substituents represented by $R^{C3}$ to $R^{C6}$ in the general formula (11).

The compound represented by the general formula (1) is particularly preferably represented by the following general formula (13).

[Chem. 11]

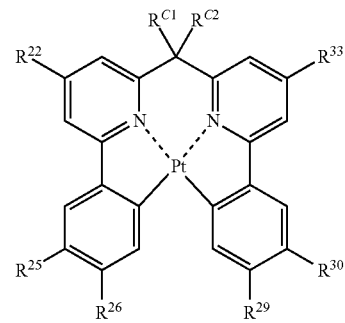

General Formula (13)

In the general formula (13), $R^{C1}$ and $R^{C2}$ have the same definitions as $R^{C1}$ and $R^{C2}$ in the general formula (1), and $R^{22}$, $R^{25}$, $R^{26}$, $R^{29}$, $R^{30}$, and $R^{33}$ each independently represent a hydrogen atom or a substituent.

The preferred ranges of $R^{22}$ and $R^{33}$ are each the same as the preferred ranges of $R^{12}$ and $R^{23}$ in the general formula (12), and each more preferably a hydrogen atom.

The preferred ranges of $R^{25}$ and $R^{30}$ are each the same as the preferred ranges of $R^{15}$ and $R^{20}$ in the general formula (12), and more preferably a hydrogen atom or a phenyl group.

The preferred ranges of $R^{26}$ and $R^{29}$ are each the same as the preferred ranges of $R^{16}$ and $R^{19}$ in the general formula (12), and more preferably a hydrogen atom.

Specific examples of the compound represented by the general formula (1) are shown below, but it should not be construed that the compound represented by the general formula (1) which can be used in the present invention is limited to these specific examples.

[Chem. 12]

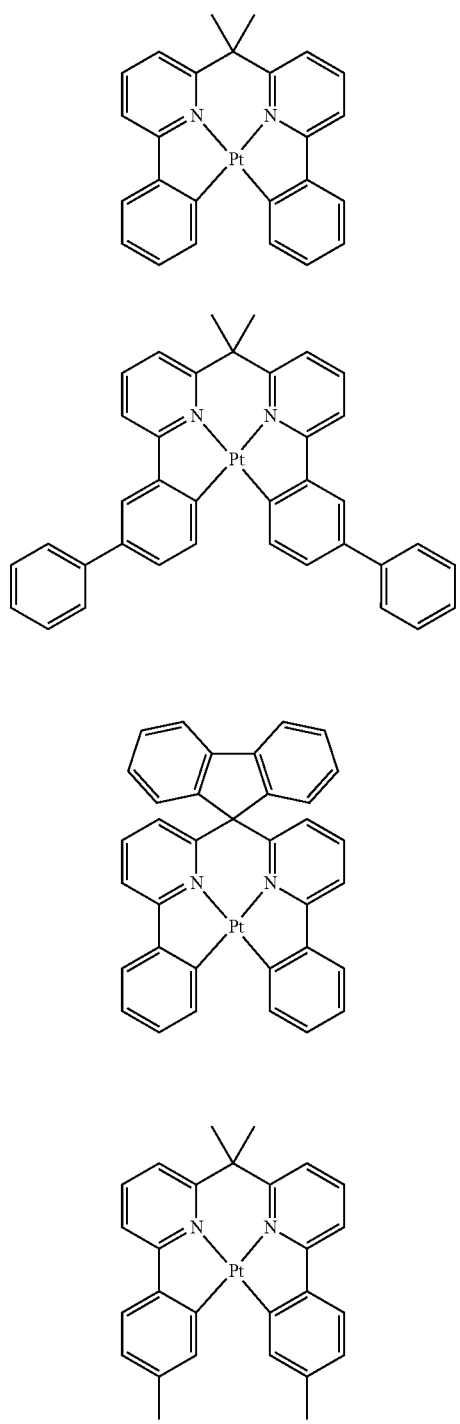

(Pt-1)

(Pt-2)

(Pt-3)

(Pt-4)

-continued

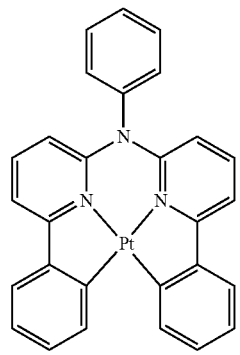

(Pt-5)

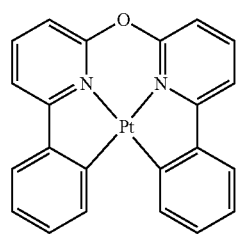

(Pt-6)

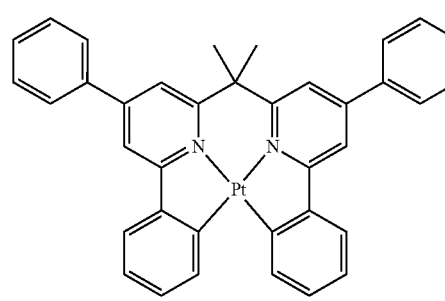

(Pt-7)

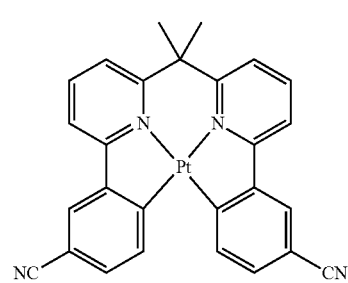

(Pt-8)

[Chem. 13]

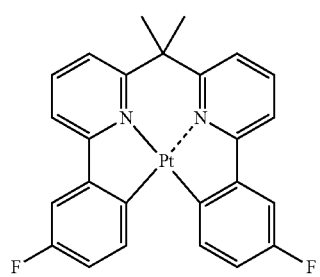

Pt-9

-continued
Pt-10
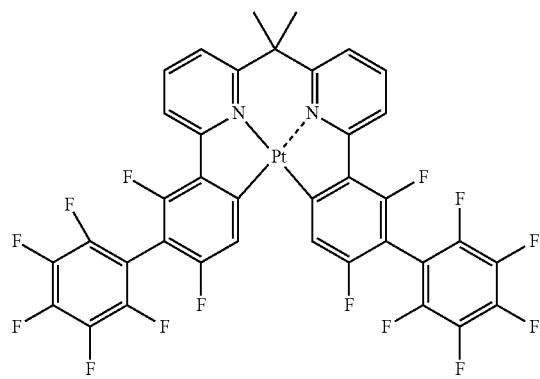
Pt-11
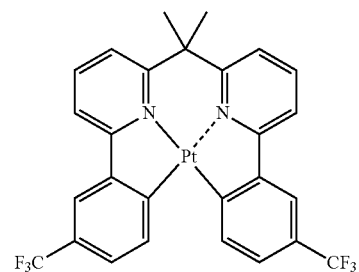
Pt-12
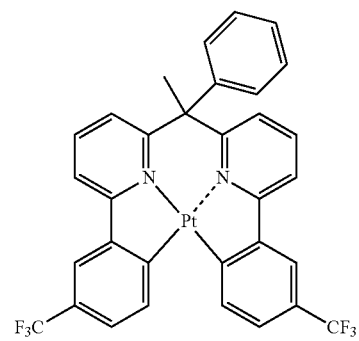
Pt-13
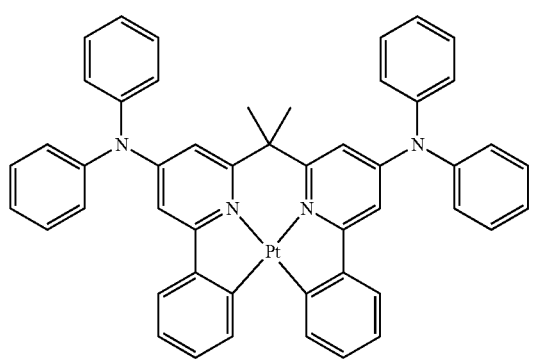
-continued
Pt-14
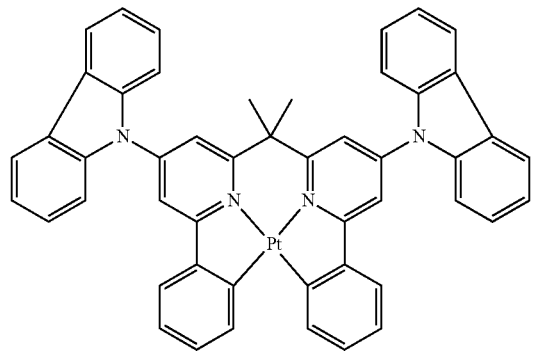
Pt-15
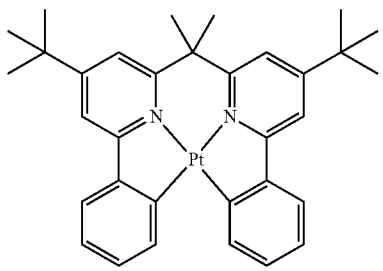
Pt-16
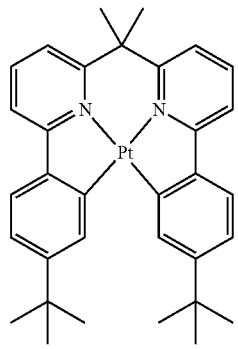
Pt-17
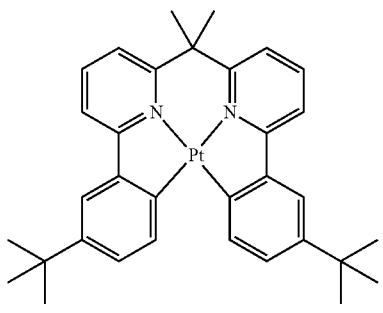
Pt-18
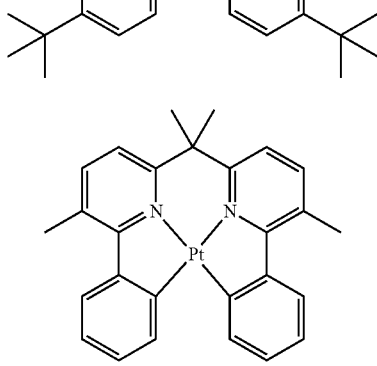

Pt-19
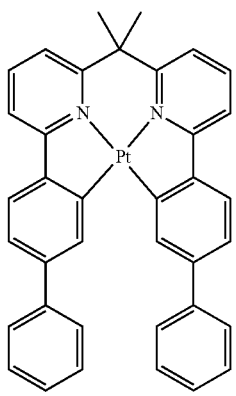

Pt-20
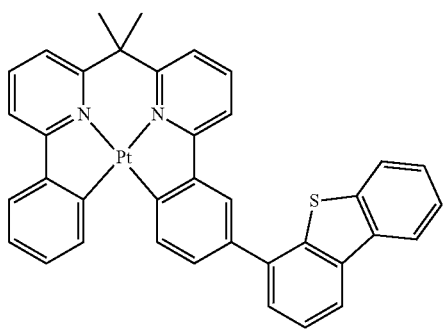

[Chem. 14]

Pt-22
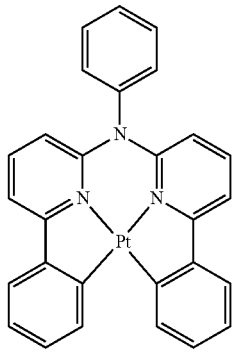

Pt-23
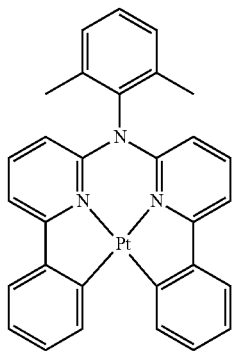

Pt-24
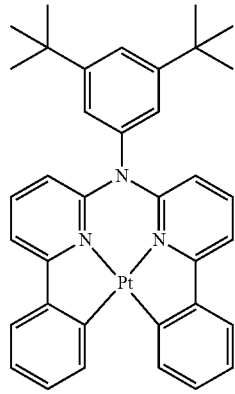

Pt-25
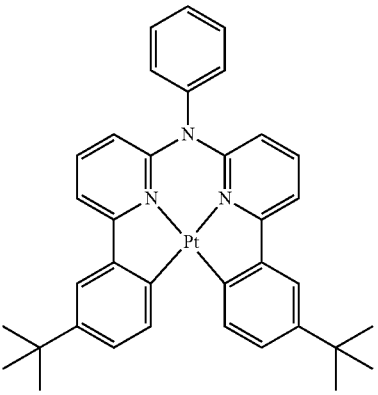

Pt-26
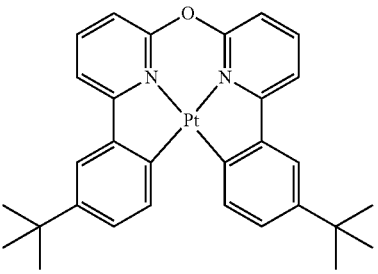

The compound represented by the general formula (1) can be synthesized by various methods, for example, the method described on line 53 in the left column to line 7 in the right column on page 789, the method described on lines 18 to 38 in the left column on page 790, and the method described on lines 19 to 30 in the right column on page 790, of Journal of Organic Chemistry 53, 786, (1988), G. R. Newkome et al.), and a combination thereof, and the method described on lines 26 to 35 on page 2752 of Chemische Berichte 113, 2749 (1980), H. Lexy, et al.).

For example, the compound can also be obtained at a temperature no higher than room temperature or by heating (for which a method using heating with microwaves is effective in addition to common heating) a ligand or a dissociated form thereof and a metal compound in the presence of a solvent (for example, a halogen-based solvent, an alcohol-based solvent, an ether-based solvent, an ester-based solvent, a ketone-based solvent, a nitrile-based solvent, an amide-based solvent, a sulfone-based solvent, a sulfoxide-based solvent, and water) or in the absence of a solvent, in the presence of a base (including various inorganic or organic bases, for example, sodium methoxide, t-butoxypotassium, triethylamine, and potassium carbonate), or in the absence of a base.

The content of the compound represented by the general formula (1) in the light emitting layer of the organic electroluminescent element of the present invention is preferably from 1% by mass to 30% by mass, more preferably from 3% by mass to 25% by mass, and still more preferably from 5% by mass to 20% by mass in the light emitting layer.

<Host Material Represented by General Formula (H-1)>

In the organic electroluminescent element of the present invention, the light emitting layer contains at least one kind of host material represented by the following general formula (H-1).

[Chem. 15]

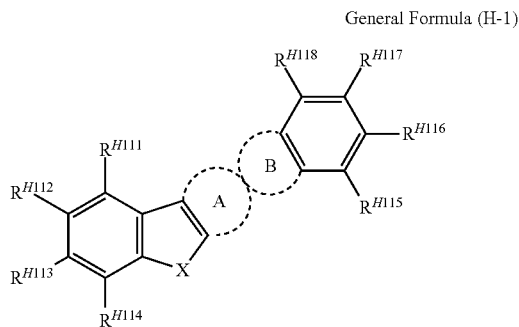

General Formula (H-1)

(In the general formula (H-1), $R^{H111}$ to $R^{H118}$ each independently represent a hydrogen atom or a substituent, X represents any one of O, S, $NR^{H119}$, $CR^{H120}R^{H121}$, and $SiR^{H122}R^{H123}$, and $R^{H119}$ to $R^{H123}$ each independently represent a substituent. The ring A represents a benzene ring and the ring B represents a 5- or 6-membered ring.)

In the general formula (H-1), $R^{H111}$ to $R^{H118}$ each independently represent a hydrogen atom or a substituent.

$R^{H111}$ to $R^{H118}$ are each independently preferably a hydrogen atom, an alkyl group, an aryl group, a silyl group, a fluorine atom, a cyano group, or a trifluoromethyl group, and these groups may be further substituted, if possible, with at least one selected from an alkyl group having 1 to 6 carbon atoms, and a phenyl group. $R^{H111}$ to $R^{H118}$ are more preferably a hydrogen atom or an aryl group, and particularly preferably a hydrogen atom.

In the general formula (H-1), X represents any one of O, S, $NR^{H119}$, $CR^{H120}R^{H121}$, and $SiR^{H122}R^{H123}$, and $R^{H119}$ to $R^{H123}$ each independently represent a substituent.

Examples of the substituent represented by $R^{H119}$ each independently include the substituents in the Substituent Group B in the description of the general formula (1), and above all, a benzene ring, a pyridine ring, a triazine ring, or a pyrimidine ring group is preferred. Such a ring may be further substituted with at least one group selected from a methyl group, an isobutyl group, a t-butyl group, a neopentyl group, a phenyl group, a naphthyl group, a cyano group, and a fluorine atom, or a triazine ring or pyrimidine ring group. The substituent represented by $R^{H119}$ is more preferably a benzene ring group (which means a substituted or unsubstituted phenyl group).

Examples of the substituents represented by $R^{H120}$ to $R^{H123}$ include the substituents in the Substituent Group A in the description of the general formula (1), and above all, for example, an alkyl group and an aryl group are preferred.

In the general formula (H-1), X is more preferably $NR^{H119}$.

In the general formula (H-1), the ring B represents a 5- or 6-membered ring, and also represents a 5- or 6-membered ring which can be fused with an adjacent ring. The 5-membered ring or the 6-membered ring represented by the ring B is not particularly limited, but a 5-membered ring is preferred, and a 5-membered ring which is a hydrocarbon ring or a 5-membered ring containing one hetero atom (in which the hetero atom is preferably an oxygen atom, a sulfur atom, a nitrogen atom, or a silicon atom) is more preferred.

In the general formula (H-1), the ring A represents a benzene ring, and may have an additional substituent. Examples of the substituent which the ring A may have each independently include the substituents in the Substituent Group A in the description of the general formula (1), and above all, for example, an alkyl group and an aryl group are preferred.

The ring A is preferably an unsubstituted benzene ring.

In the general formula (H-1), the linking mode between the ring A and the ring B is not particularly limited, except that they form a fused ring, but the host material represented by the general formula (H-1) is preferably represented by any one of the following general formulae (H-2), (H-3), (H-4), and (H-5).

[Chem. 16]

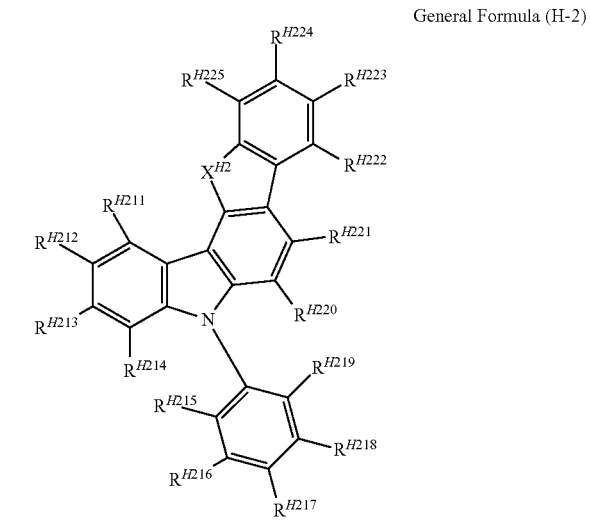

General Formula (H-2)

In the general formula (H-2), $R^{H211}$ to $R^{H225}$ each independently represent a hydrogen atom or a substituent, and $X^{H2}$ represents either of O and S.

The preferred ranges of $R^{H211}$ to $R^{H214}$ and $R^{H222}$ to $R^{H225}$ are the same as the preferred ranges of $R^{H111}$ to $R^{H118}$ in the general formula (H-1).

The preferred ranges of $R^{H220}$ and $R^{H221}$ are each a hydrogen atom or the ranges of the substituents which the ring A may have in the general formula (H-1), and a hydrogen atom is more preferred.

In the case where $R^{H215}$ to $R^{H219}$ each represent a substituent, examples of the substituent include the substituents which $R^{H119}$ in the general formula (H-1) may have, and above all, a phenyl group, a triazine ring, or a pyrimidine ring group is preferred, a phenyl group or a pyrimidine ring group is more preferred, and a phenyl group is particularly preferred.

$R^{H215}$ to $R^{H219}$ may have an additional substituent, and the substituent is preferably an aryl group (which may have an additional substituent), more preferably a phenyl group, a biphenyl group, a p-terphenyl group, or an m-terphenyl group, particularly preferably a phenyl group or a p-terphenyl group, and more particularly preferably a p-terphenyl group.

In the case where $R^{H215}$ to $R^{H219}$ have an additional substituent, the substituent is preferably one connected with a meta position with respect to a benzene ring having $R^{H215}$ to $R^{H219}$.

In $R^{H215}$ to $R^{H219}$, the number of the substituents is preferably 1 to 2, and more preferably 1. Further, among $R^{H215}$ to $R^{H219}$, it is preferable that $R^{H218}$ or $R^{H217}$ be a substituent, and it is more preferable that $R^{H218}$ be a substituent.

[Chem. 17]

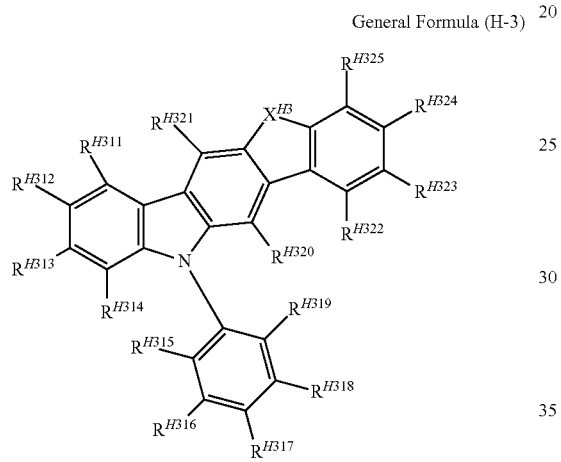

General Formula (H-3)

In the general formula (H-3), $R^{H311}$ to $R^{H325}$ each independently represent a hydrogen atom or a substituent, and $X^{H3}$ represents either of O and S.

The preferred ranges of $R^{H311}$ to $R^{H314}$ and $R^{H322}$ to $R^{H325}$ are the same as the preferred ranges of $R^{H111}$ to $R^{H118}$ in the general formula (H-1).

The preferred ranges of $R^{H320}$ and $R^{H321}$ are a hydrogen atom or the ranges of the substituent which the ring A in the general formula (H-1) may have, and a hydrogen atom is more preferred.

In the case where $R^{H315}$ to $R^{H319}$ represent a substituent, examples of the substituent include the substituents which $R^{H119}$ in the general formula (H-1) may have, and above all, a phenyl group, a triazine ring, or a pyrimidine ring group is preferred, a phenyl group or a triazine ring group is more preferred, and a phenyl group is particularly preferred.

$R^{H315}$ to $R^{H319}$ may have an additional substituent, and the substituent is preferably an aryl group (which may have an additional substituent), more preferably a phenyl group, a biphenyl group, a p-terphenyl group, or an m-terphenyl group, particularly preferably a phenyl group or a p-terphenyl group, and more particularly preferably a p-terphenyl group.

In the case where $R^{H315}$ to $R^{H319}$ have an additional substituent, the substituent is preferably one connected with a meta position with respect to a benzene ring having $R^{H315}$ to $R^{H319}$.

In $R^{H315}$ to $R^{H319}$, the number of the substituents is preferably 1 to 2, and more preferably 1. Further, among $R^{H315}$ to $R^{H319}$, it is preferable that $R^{H318}$ or $R^{H317}$ be a substituent, and it is more preferable that $R^{H318}$ be a substituent.

[Chem. 18]

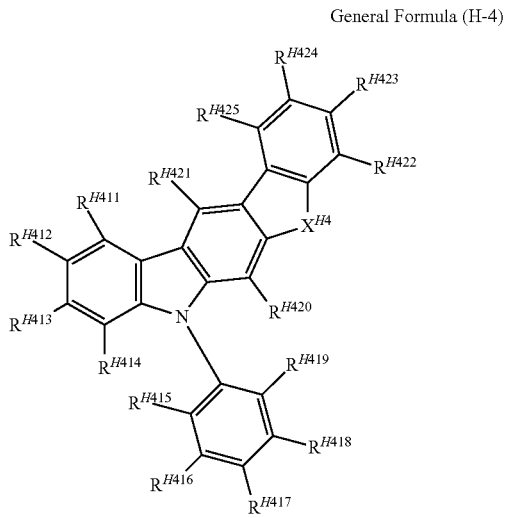

General Formula (H-4)

In the general formula (H-4), $R^{H411}$ to $R^{H425}$ each independently represent a hydrogen atom or a substituent, $X^{H4}$ represents any one of O, S, $NR^{H426}$, $CR^{H427}R^{H428}$, and $SiR^{H429}R^{H430}$, and $R^{H426}$ to $R^{H430}$ each independently represent a hydrogen atom or a substituent.

The preferred ranges of $R^{H411}$ to $R^{H414}$ and $R^{H422}$ to $R^{H425}$ are the same as the preferred ranges of $R^{H111}$ to $R^{H118}$ in the general formula (H-1).

The preferred ranges of $R^{H420}$ and $R^{H421}$ are a hydrogen atom or the ranges of the substituent which the ring A in the general formula (H-1) may have, and a hydrogen atom is more preferred.

In the case where $R^{H415}$ to $R^{H419}$ represent a substituent, examples of the substituent include the substituents which $R^{H119}$ in the general formula (H-1) may have, and above all, a phenyl group, a triazine ring, or a pyrimidine ring group is preferred, a phenyl group or a pyrimidine ring group is more preferred, and a phenyl group is particularly preferred.

$R^{H415}$ to $R^{H419}$ may have an additional substituent, and the substituent is preferably an aryl group (which may have an additional substituent), more preferably a biphenyl group, a p-terphenyl group, or an m-terphenyl group, particularly preferably a phenyl group or a p-terphenyl group, and more particularly preferably a p-terphenyl group.

In the case where $R^{H415}$ to $R^{H419}$ have an additional substituent, the substituent is preferably one connected with a meta position with respect to a benzene ring having $R^{H415}$ to $R^{H419}$.

In $R^{H415}$ to $R^{H419}$, the number of the substituents is preferably 0 to 2, and more preferably 0. Further, in the case where $R^{H415}$ to $R^{H419}$ have a substituent, the substituent is preferably an alkyl group or an aryl group.

$X^{H4}$ represents any one of O, S, $NR^{H426}$, $CR^{H427}R^{H428}$, and $SiR^{H429}R^{H430}$, and $R^{H426}$ to $R^{H430}$ each independently represent a hydrogen atom or a substituent.

$R^{H426}$ to $R^{H430}$ each independently represent a hydrogen atom or a substituent, and preferably a substituent.

Examples of the substituent represented by $R^{H426}$ include the substituents in the Substituent Group B in the description of the general formula (1), and above all, a benzene ring, a pyridine ring, a triazine ring, or a pyrimidine ring group is preferred. Such a ring may be further substituted with at least one group selected from a methyl group, an isobutyl group, a t-butyl group, a neopentyl group, a phenyl group, a naphthyl group, a cyano group, and a fluorine atom, or a triazine ring, pyrimidine ring, or carbazole ring (the carbazole ring may have an additional substituent) group. The substituent represented by $R^{H426}$ is more preferably a benzene ring group (which means a substituted or unsubstituted phenyl group) or a triazine ring group, and particularly preferably a benzene ring group.

The benzene ring group represented by $R^{H426}$ may have an additional substituent, and the preferred range of the kind, the number of the substituent are the same as the preferred range of the kind, the number of the substituents represented by $R^{H215}$ to $R^{H219}$ in the description of the general formula (H-2).

The triazine ring group represented by $R^{H426}$ may have an additional substituent, and as the additional substituent which the triazine ring group has, an aryl group or a carbazole ring (the carbazole ring may have an additional substituent) group is preferred, a phenyl group or a carbazole ring group having a substituent (it is preferable that the substituent be a dibenzylamino group, and it is more preferable that the dibenzylamino group be bonded to the carbazole ring to form a fused ring). The number of the additional substituents which the triazine ring group has is preferably 1 or 2, and more preferably 2, with respect to the triazine ring group.

The preferred ranges of the substituents represented by $R^{H427}$ to $R^{H430}$ are the same as the preferred ranges of the substituents represented by $R^{H120}$ to $R^{H123}$ in the description of the general formula (H-1).

[Chem. 19]

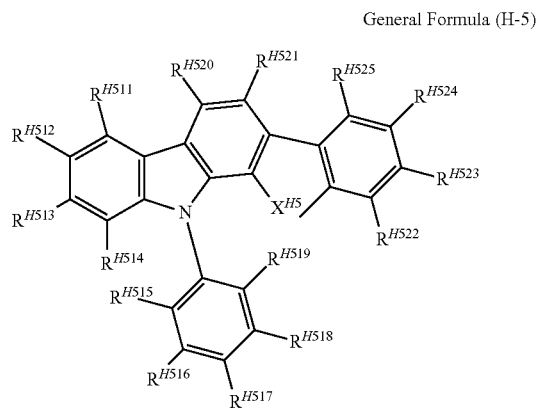

General Formula (H-5)

In the general formula (H-5), $R^{H511}$ to $R^{H525}$ each independently represent a hydrogen atom or a substituent, and $X^{H5}$ represents any one of O, S, $NR^{H526}$, $CR^{H527}R^{H528}$, and $SiR^{H529}R^{H530}$, and $R^{H526}$ to $R^{H530}$ each independently represent a hydrogen atom or a substituent.

The preferred ranges of $R^{H511}$ to $R^{H514}$ and $R^{H522}$ to $R^{H525}$ are the same as the preferred ranges of $R^{H111}$ to $R^{H118}$ in the general formula (H-1).

The preferred ranges of $R^{H520}$ and $R^{H521}$ are a hydrogen atom or the ranges of the substituent which the ring A in the general formula (H-1) may have, and a hydrogen atom is preferred.

In the case where $R^{H515}$ to $R^{H519}$ represent a substituent, examples of the substituent include the substituents which $R^{H119}$ in the general formula (H-1) may have, and above all, a phenyl group, a triazine ring, or a pyrimidine ring group is preferred, a phenyl group or a pyrimidine ring group is more preferred, and a phenyl group is particularly preferred.

$R^{H515}$ to $R^{H519}$ may have an additional substituent, and the substituent is preferably an aryl group (which may have an additional substituent), more preferably a biphenyl group, a p-terphenyl group, or an m-terphenyl group, particularly preferably a phenyl group or a p-terphenyl group, and more particularly preferably a p-terphenyl group.

In the case where $R^{H515}$ to $R^{H519}$ have an additional substituent, the substituent is preferably one connected with a meta position with respect to a benzene ring having $R^{H515}$ to $R^{H519}$.

In $R^{H515}$ to $R^{H519}$, the number of the substituents is preferably 0 to 2, and more preferably 0. Further, in the case where $R^{H515}$ to $R^{H519}$ have a substituent, the substituent is preferably an alkyl group or an aryl group.

$X^{H5}$ represents any one of O, S, $NR^{H526}$, $CR^{H527}R^{H528}$, and $SiR^{H529}R^{H530}$, and preferably $NR^{H526}$.

$R^{H526}$ to $R^{H530}$ each independently represent a hydrogen atom or a substituent, and preferably a substituent.

Examples of the substituent represented by $R^{H526}$ include the substituents in the Substituent Group Bin the description of the general formula (1), and above all, a benzene ring, a pyridine ring, a triazine ring, or a pyrimidine ring group is preferred. Such a ring may be further substituted with at least one group selected from a methyl group, an isobutyl group, a t-butyl group, a neopentyl group, a phenyl group, a naphthyl group, a cyano group, and a fluorine atom, or a triazine ring, pyrimidine ring, or carbazole ring (the carbazole ring may have an additional substituent) group. The substituent represented by $R^{H526}$ is more preferably a benzene ring group (which means a substituted or unsubstituted phenyl group) or a triazine ring group, and particularly preferably a benzene ring group.

The benzene ring group represented by $R^{H526}$ may have an additional substituent, and the preferred range of the kind, the number of the substituent are the same as the preferred range of the kind, the number of the substituents represented by $R^{H215}$ to $R^{H219}$ in the description of the general formula (H-2).

The triazine ring group represented by $R^{H526}$ may have an additional substituent, and as the additional substituent which the triazine ring group has, an aryl group or a carbazole ring (the carbazole ring may have an additional substituent) group is preferred, a phenyl group or a carbazole ring group having a substituent (it is preferable that the substituent be a dibenzylamino group, and it is more preferable that the dibenzylamino group be bonded to the carbazole ring to form a fused ring). The number of the additional substituents which the triazine ring group has is preferably 1 or 2, and more preferably 2, with respect to the triazine ring group.

The preferred ranges of the substituents represented by $R^{H527}$ to $R^{H530}$ are the same as the preferred ranges of the substituents represented by $R^{H120}$ to $R^{H123}$ in the description of the general formula (H-1).

For the organic electroluminescent element of the present invention, the host material represented by the general formula (H-1) is preferably represented by the general formula (H-2) or (H-5) from the viewpoint of easiness of synthesis, and is more preferably represented by the general formula (H-2).

On the other hand, for the organic electroluminescent element of the present invention, the host material represented by the general formula (H-1) is more preferably represented by the general formula (H-2), (H-3), or (H-4) from the viewpoint of luminous efficiency and durability, and still more preferably represented by the general formula (H-2) or (H-4).

Specific examples of the compound represented by the general formula (H-1) are shown below, but it should not be construed that the compound represented by the general formula (H-1) which can be used in the present invention is limited to these specific examples.

Furthermore, as the compound represented by the general formula (H-1), the compounds described in paragraph Nos. [0279] to [0303] of JP-A-2011-91355, the compounds described in WO2011/057701, the compounds described in WO2009/148062, the compounds described in WO2011/010844, the compounds described in WO2010/131855, or the like can be used.

[Chem. 20]

(EH-1)

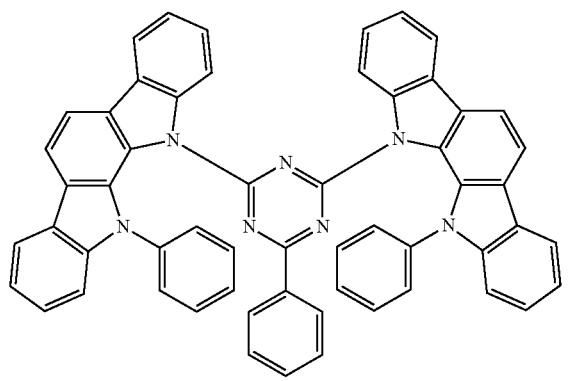

(EH-2)

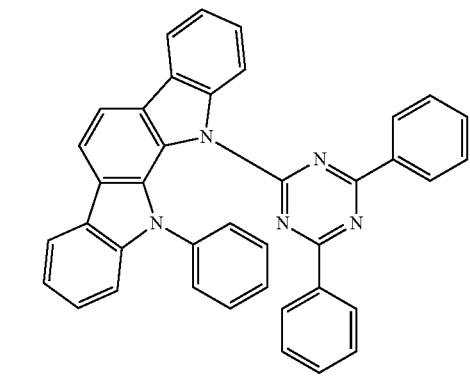

(EH-3)

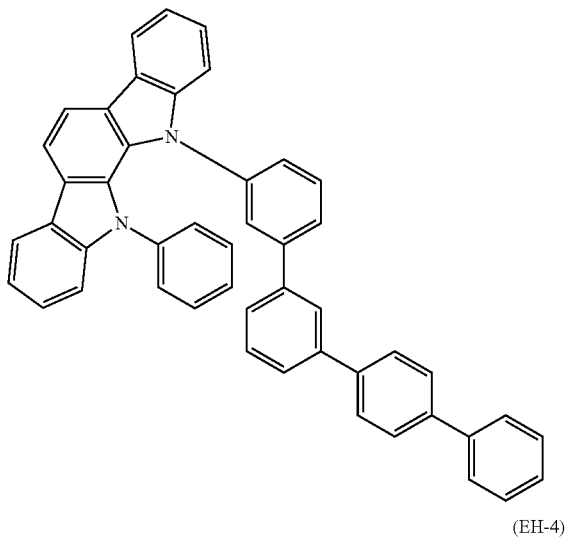

(EH-4)

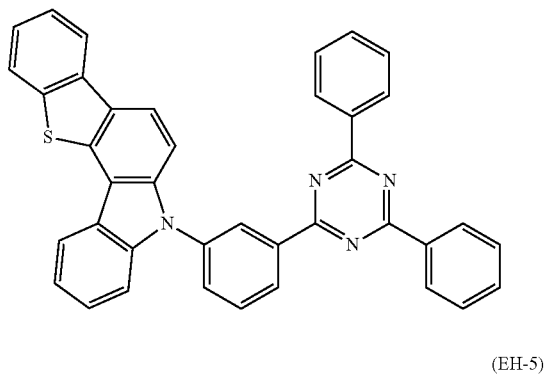

(EH-5)

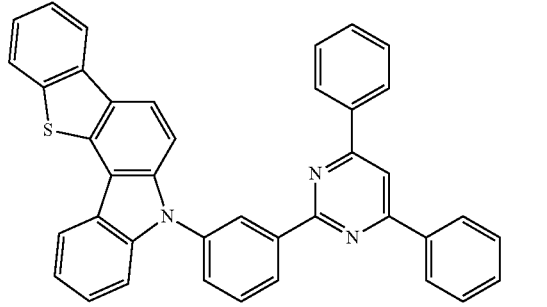

(EH-6)

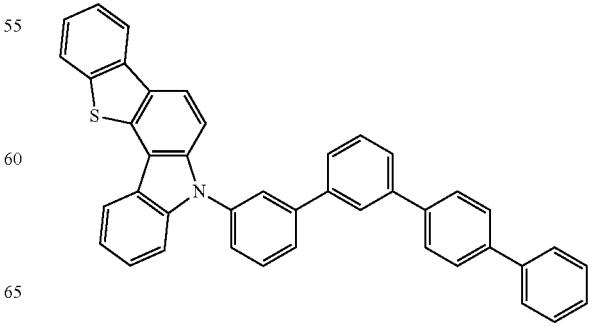

(EH-7)
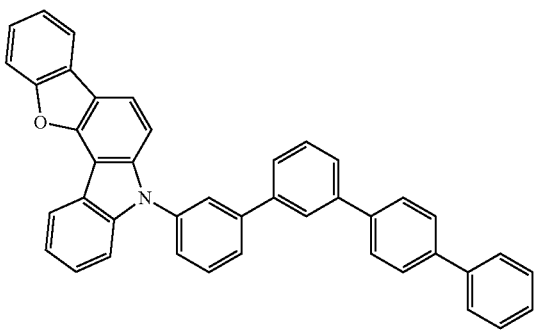
[Chem. 21]
(EH-8)
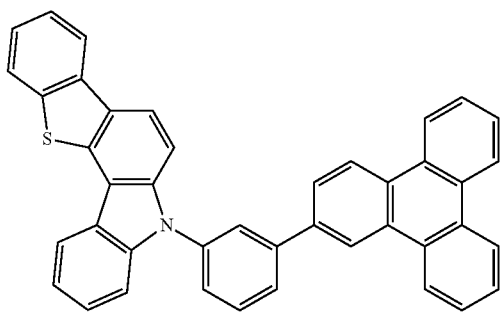
(EH-9)
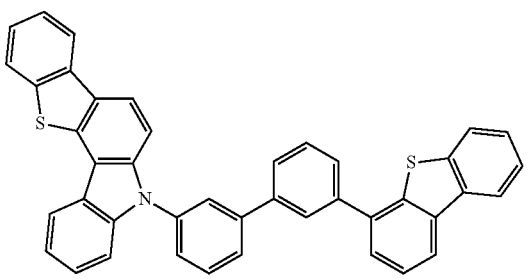
(EH-10)
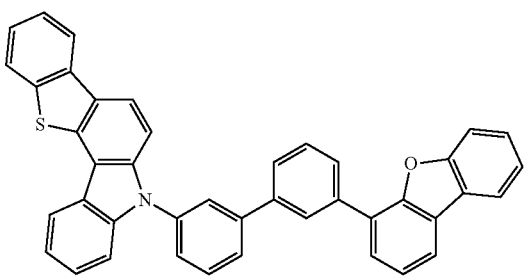
(EH-11)
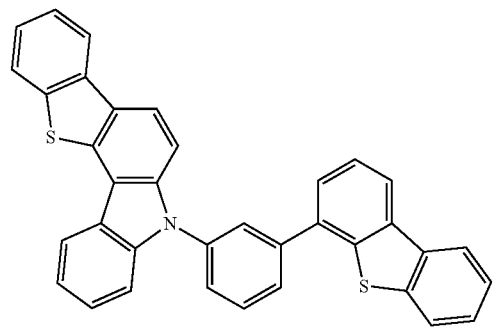
(EH-12)
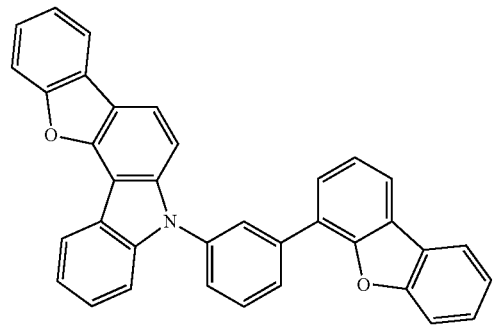
(EH-13)
(EH-14)
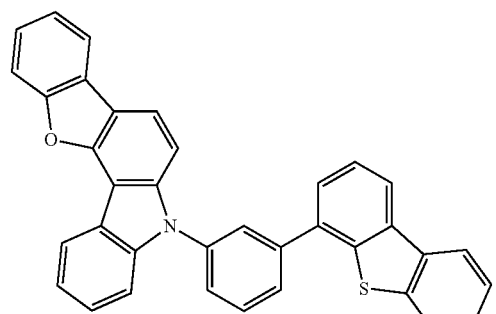

(EH-15)
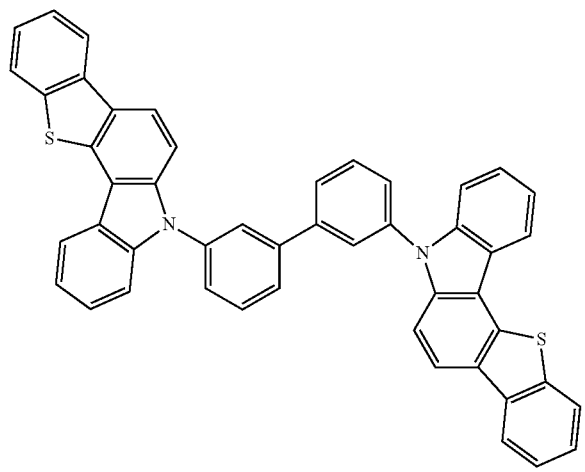
(EH-16)
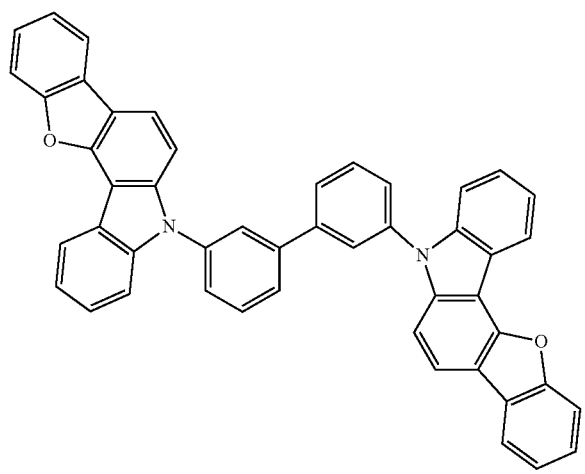
(EH-17)
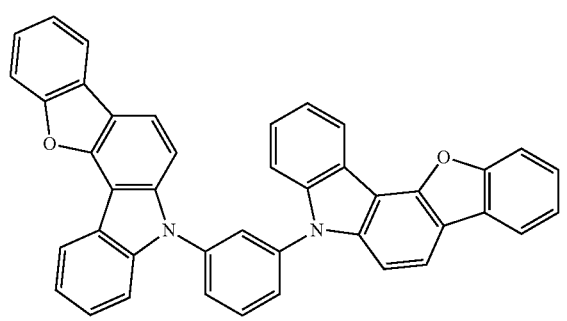
(EH-18)
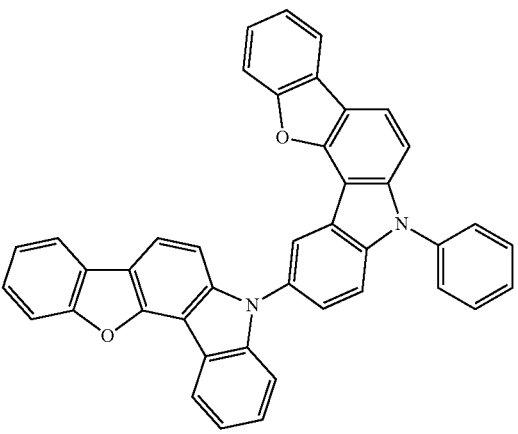
(EH-19)
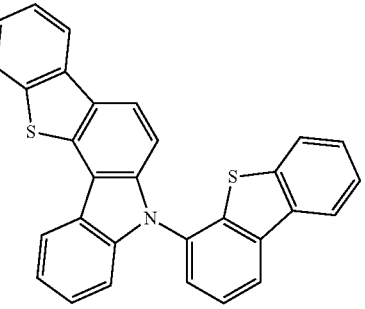
[Chem. 22]
(EH-20)
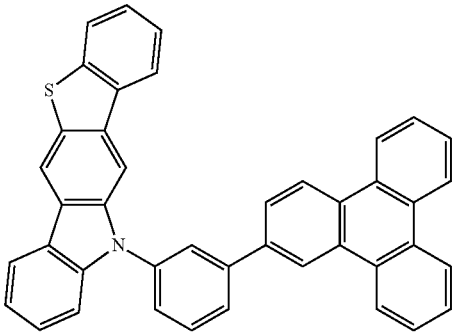
(EH-21)
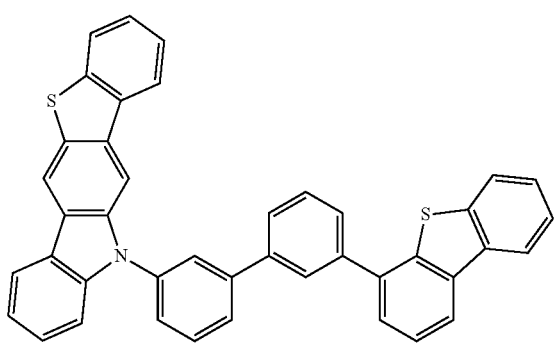

(EH-22)
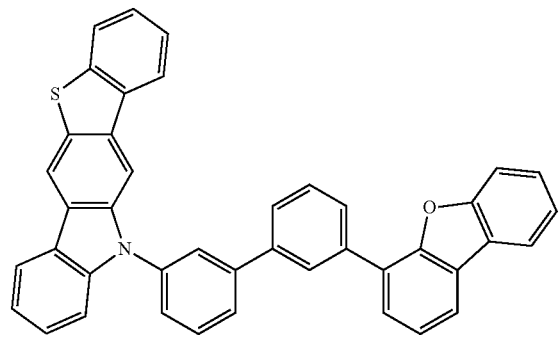
(EH-23)
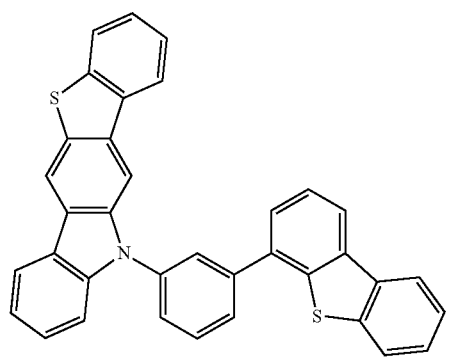
(EH-24)
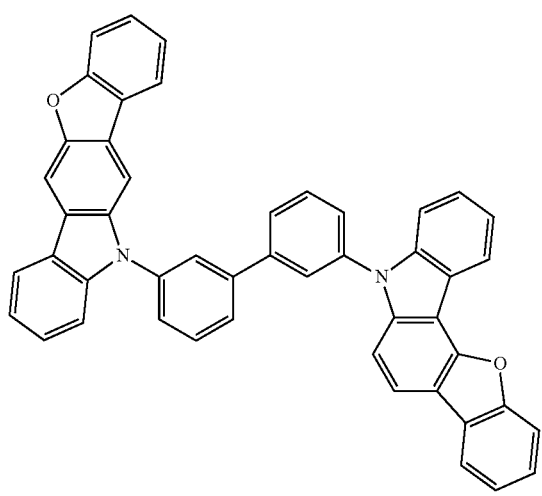
(EH-25)
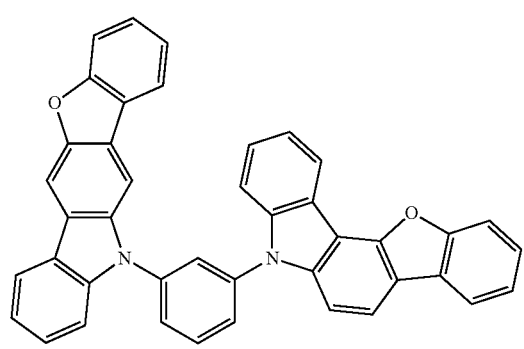
(EH-26)
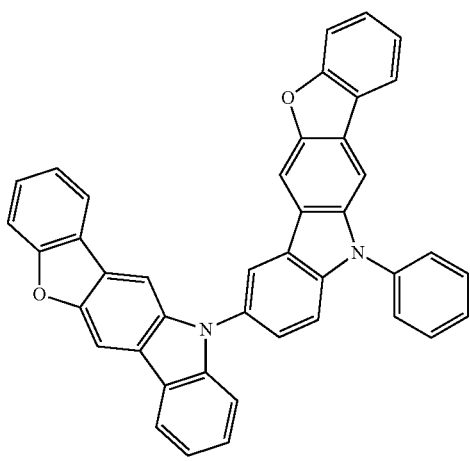
(EH-27)
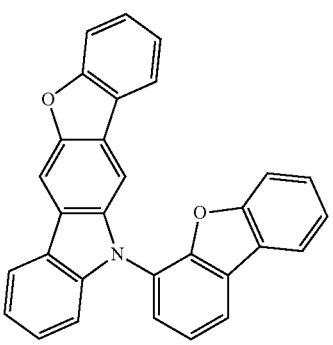
(EH-28)
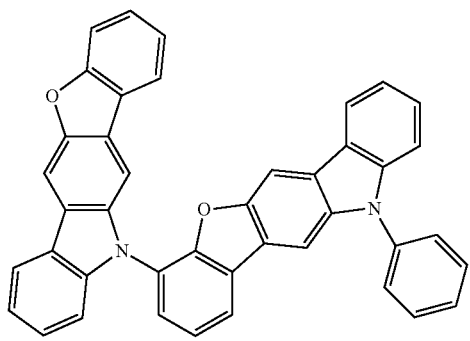
(EH-29)
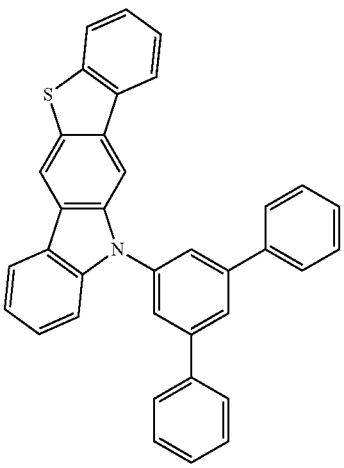

(EH-30)
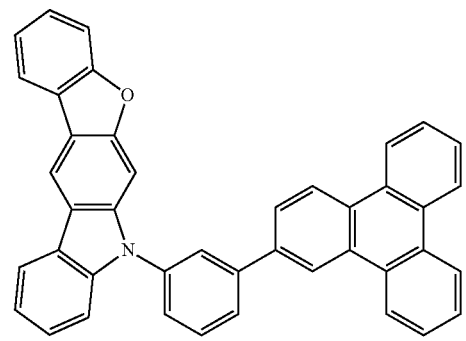
(EH-31)
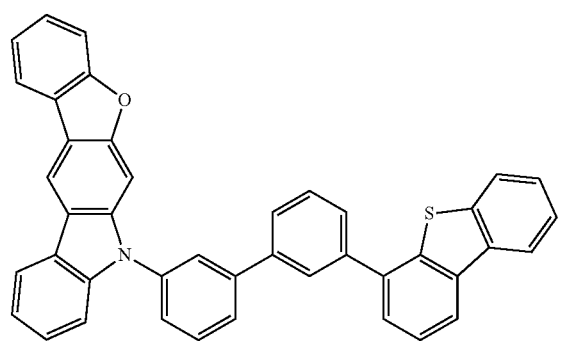
(EH-32)
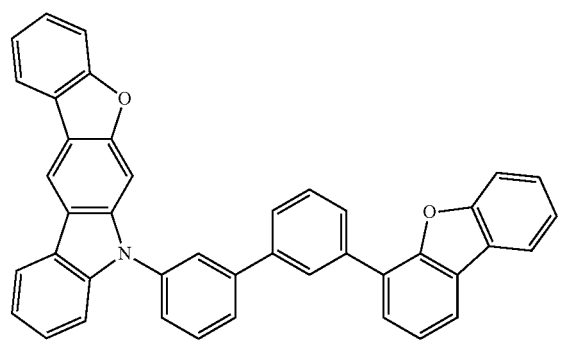
(EH-33)
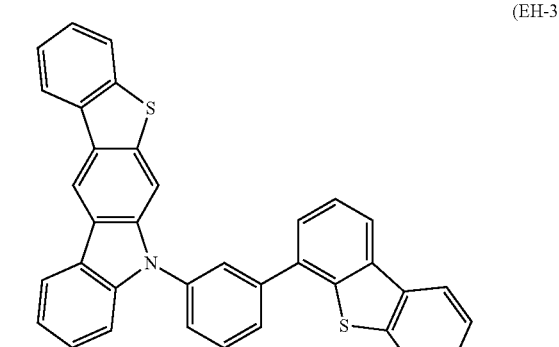
(EH-34)
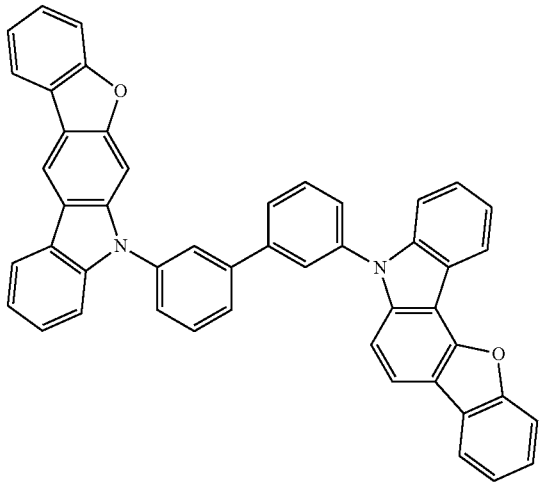
(EH-35)
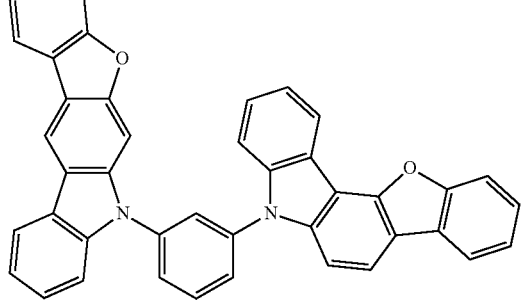
(EH-36)
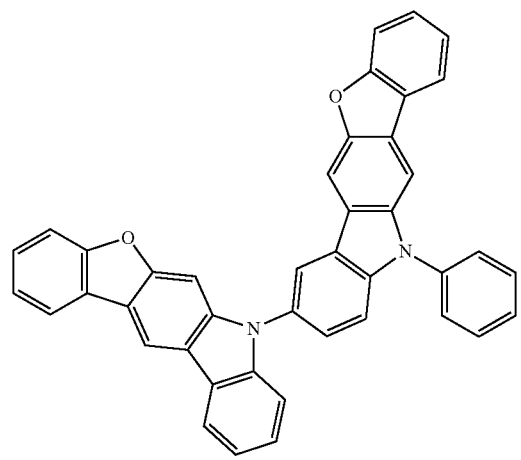

(EH-37)
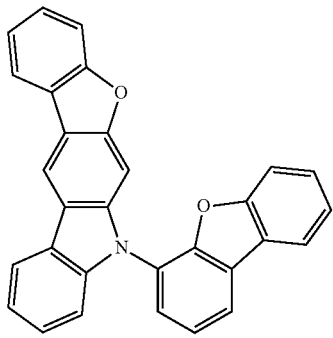
(EH-38)
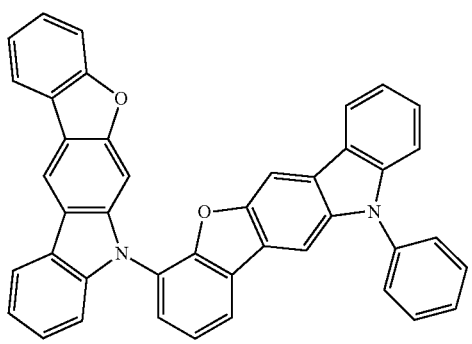
(EH-39)
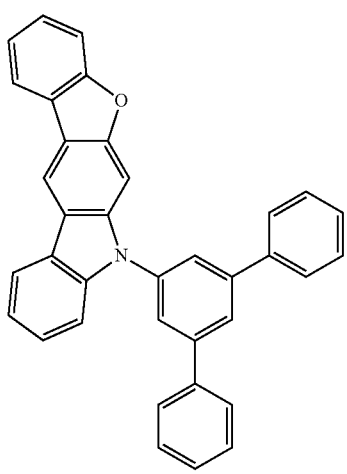
[Chem. 24]
(EH-40)
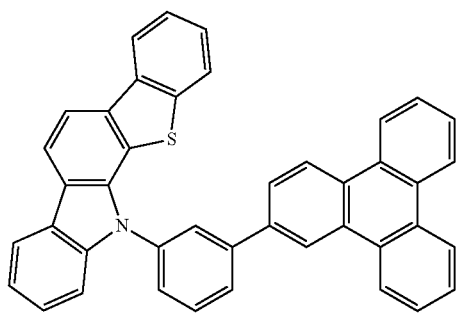
(EH-41)
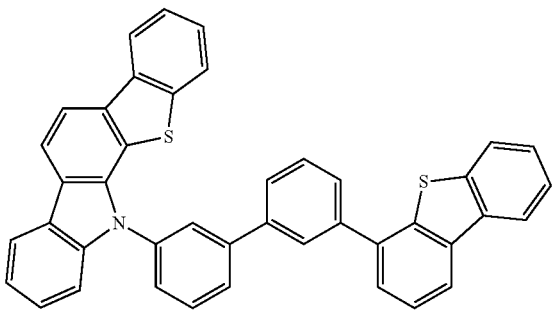
(EH-42)
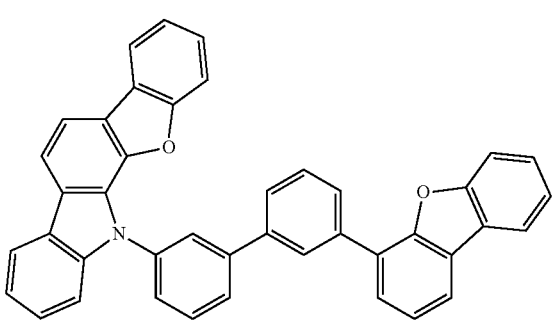
(EH-43)
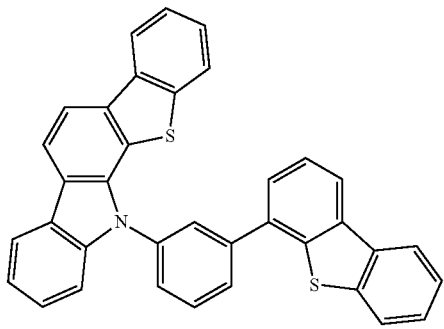
(EH-44)
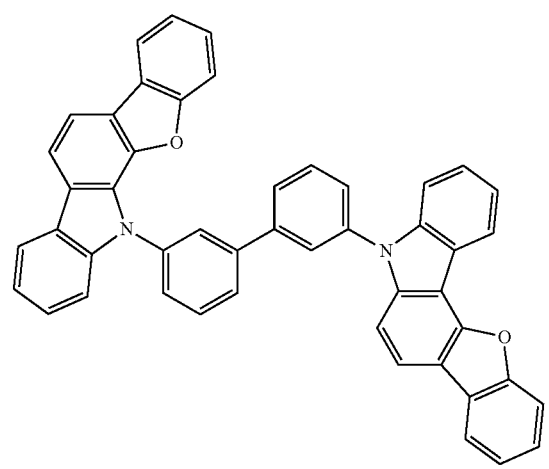

-continued (EH-45)

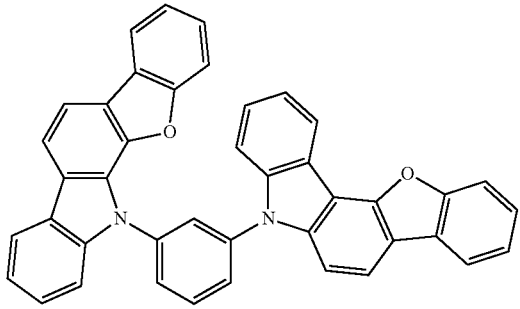

(EH-46)

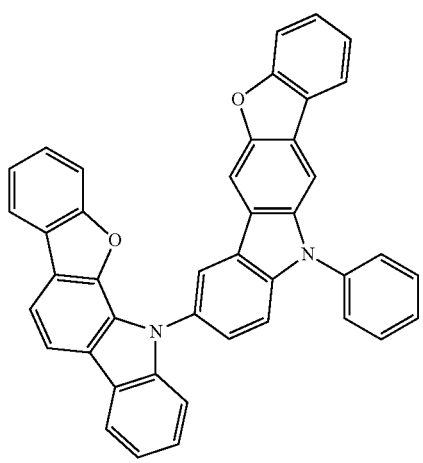

(EH-47)

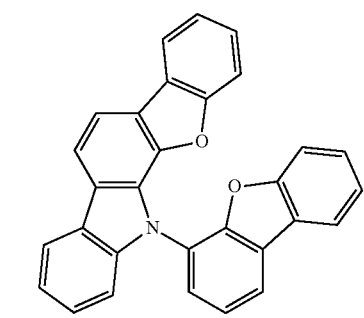

(EH-48)

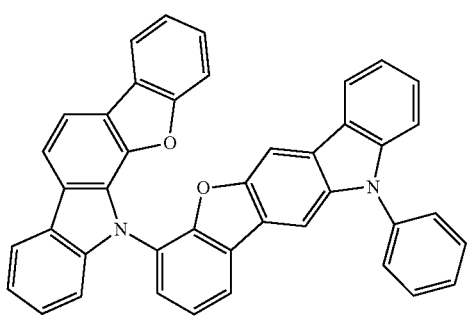

-continued (EH-49)

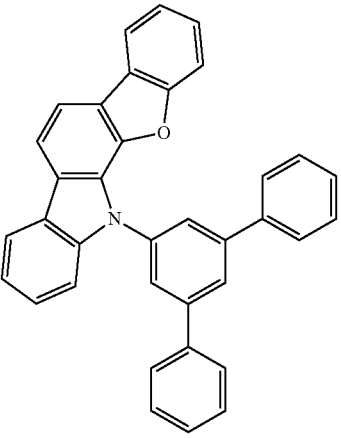

The compound represented by the general formula (H-1) can be easily prepared by a known method. For example, the compound can be prepared with reference to Synthesis Examples shown in Tetrahedron, 47, 7739-7750 (1991), Synlett, 42-48 (2005), Synthesis Examples described in WO2010/131855 or JP-A-2011-91355, or the like.

The compound represented by the general formula (H-1) is contained in the amount of preferably 10% by mass to 99% by mass, more preferably 30% by mass to 97% by mass, and still more preferably 50% by mass to 95% by mass, and more particularly preferably 60% by mass to 95% by mass, with respect to the total mass of the light emitting layer.

Furthermore, if the purity of the compound represented by the general formula (H-1) is low, the impurities serve as a trap for charge transportation or promote the deterioration of an element, and therefore, a higher purity of the compound represented by the general formula (H-1) is more preferred. The purity can be measured by, for example, high performance liquid chromatography (HPLC), and the area ratio of the compound represented by the general formula (H-1), as detected at light absorption intensity of 254 nm, is preferably 95.0% or more, more preferably 97.0% or more, particularly preferably 99.0% or more, and most preferably 99.9% or more. Examples of a method for increasing the purity of the compound represented by the general formula (H-1) include sublimation purification.

[Configuration of Organic Electroluminescent Element]

The organic electroluminescent element of the present invention has a substrate, a pair of electrodes including an anode and a cathode, disposed on the substrate, and at least one organic layer including a light emitting layer, disposed between the electrodes, in which the light emitting layer contains at least one kind of light emitting material represented by the general formula (1) and at least one kind of host material represented by the general formula (H-1).

The configuration of the organic electroluminescent element of the present invention is not particularly limited. FIG. 1 shows an example of the configuration of the organic electroluminescent element of the present invention. An organic electroluminescent element 10 in FIG. 1 includes organic layers between a pair of electrodes (an anode 3 and a cathode 9) on a substrate 2.

The element configuration, the substrate, the anode, and the cathode of the organic electroluminescent element are described in detail, for example, in JP-A-2008-270736, and the matters described in the patent publication can be applied to the present invention.

Hereinafter, preferred aspects of the organic electroluminescent element of the present invention will be described in detail, in the order of the substrate, the electrode, the organic layer, the protective layer, the sealing enclosure, the driving method, the light emitting wavelength, and applications thereof.

<Substrate>

The organic electroluminescent element of the present invention has a substrate.

The substrate used in the present invention is preferably a substrate that does not scatter or attenuate light emitted from the organic layer. In the case of an organic material, those having excellent heat resistance, dimensional stability, solvent resistance, electrical insulating properties, and processability are preferred.

<Electrodes>

The organic electroluminescent element of the present invention has a pair of electrodes including an anode and a cathode, disposed on the substrate.

In view of the properties of the light emitting element, at least one electrode of a pair of electrodes, the anode and the cathode, is preferably transparent or semi-transparent.

(Anode)

The anode may be typically one having a function as an electrode of supplying holes into an organic layer, and is not particularly limited in its shape, structure, size, or the like. Further, depending on the use and purpose of the light emitting element, the anode can be suitably selected from the known electrode materials. As described above, the anode is usually provided as a transparent anode.

(Cathode)

The cathode may be typically one having a function as an electrode of injecting electrons to an organic layer, and is not particularly limited in its shape, structure, size, or the like. Further, depending on the use and purpose of the light emitting element, the cathode can be suitably selected from the known electrode materials.

<Organic Layer>

The organic electroluminescent element of the present invention has at least one organic layer including a light emitting layer, disposed between the electrodes, in which the light emitting layer contains at least one kind of light emitting material represented by the general formula (1) and at least one kind of host material represented by the general formula (H-1).

The organic layer is not particularly limited and can be suitably selected depending on the use and purpose of the organic electroluminescent element. However, the organic layer is preferably formed on the transparent electrode or the semi-transparent electrode. In that case, the organic layer is formed on the entire surface or one surface of the transparent electrode or the semi-transparent electrode.

The shape, the size, the thickness, and the like of the organic layer are not particularly limited and can be suitably selected depending on the purpose.

Hereinafter, the configuration of the organic layer, the method for forming an organic layer, preferred aspects of the respective layers constituting the organic layer, and the materials used in the respective layers in the organic electroluminescent element of the present invention will be described in order.

(Configuration of Organic Layers)

In the organic electroluminescent element of the present invention, the organic layer includes a light emitting layer.

Furthermore, the organic layer preferably includes a charge transporting layer. The charge transporting layer refers to a layer in which charges move when voltage is applied to the organic electroluminescent element. Specifically, examples thereof include a hole injecting layer, a hole transporting layer, an electron blocking layer, a light emitting layer, a hole blocking layer, an electron transporting layer, and an electron injecting layer. When the charge transporting layer is a hole injecting layer, a hole transporting layer, an electron blocking layer, or a light emitting layer, it becomes possible to prepare an organic electroluminescent element with low cost and high efficiency.

The compound represented by the general formula (1) and the compound represented by the general formula (H-1) are contained in the light emitting layer in the organic layer(s) disposed between the electrodes, among the organic layer(s) disposed between the electrodes of the organic electroluminescent element.

The compound represented by the general formula (1) and the compound represented by the general formula (H-1) may be contained in other organic layer(s) of the organic electroluminescent element of the present invention. Examples of the organic layer other than the light emitting layer, which may contain the compound represented by the general formula (1) and the compound represented by the general formula (H-1), include a hole injecting layer, a hole transporting layer, an electron transporting layer, an electron injecting layer, an exciton blocking layer, and a charge blocking layer (a hole blocking layer, an electron blocking layer, or the like), preferably any one of an exciton blocking layer, a charge blocking layer, an electron transporting layer, and an electron injecting layer, and more preferably an exciton blocking layer, a charge blocking layer, or an electron transporting layer.

(Method for Forming Organic Layers)

Each of the organic layers in the organic electroluminescent element of the present invention can be suitably formed by any of dry type film forming methods such as a deposition method and a sputtering method, and wet type film forming methods (solution coating methods) such as a transfer method, a printing method, a spin coating method, and a bar coating method.

In the organic electroluminescent element of the present invention, the light emitting layer disposed between the pair of electrodes is preferably formed by a vacuum deposition process or a wet type process, and the light emitting layer disposed between the pair of electrodes is more preferably formed by deposition of a composition containing the compound represented by the general formula (1) in at least one of the layers.

(Light Emitting Layer)

The light emitting layer is a layer having a function of, upon application of an electric field, receiving holes from the anode, the hole injecting layer, or the hole transporting layer, receiving electrons from the cathode, the electron injecting layer, or the electron transporting layer, providing a recombination site of the holes and the electrons, and causing light emitting. However, the light emitting layer in the present invention is not necessarily limited to the light emitting by such a mechanism.

The light emitting layer in the organic electroluminescent element of the present invention is constituted as a mixed layer of a host material and the light emitting material. The light emitting material may be made of one kind or two or more kinds thereof. Above all, for the organic electroluminescent element of the present invention, the light emitting layer preferably contains only the light emitting material represented by the general formula (1) as a light emitting material. The host material is preferably a charge transporting material. The host material may be made of one kind or two or more kinds thereof, and may have, for example, a configuration in which an electron transporting host material and a hole transporting host material are mixed. Above all, for the organic electroluminescent element of the present invention, the light emitting layer preferably contains only the host material represented by the general formula (H-1) as a host material.

In addition, the light emitting layer may include a material which does not have a charge transporting property and does not emit light.

In addition, the light emitting layer may be made of a single layer or multiple layers of two or more layers. Each of the layers may include the same light emitting material or host material, and may also include a different material in every layer. In the case where a plurality of light emitting layers are present, each of the light emitting layers may emit light in a different luminous color from each other.

The thickness of the light emitting layer is not particularly limited, but it is preferably from 2 nm to 500 nm, and above all, from the viewpoint of external quantum efficiency, it is more preferably from 3 nm to 200 nm, and still more preferably from 5 nm to 100 nm.

(Light Emitting Material)

In the organic electroluminescent element of the present invention, the compound represented by the general formula (1) is used as the light emitting material, but even in this case, it is possible to use the compound represented by the general formula (1) in combination with the light emitting materials different from the compound.

Other light emitting materials which can be used in the present invention may be any one of a phosphorescent light emitting material, a fluorescent light emitting material, and the like. In addition, the light emitting layer in the present invention can contain two or more kinds of light emitting materials in order to improve the color purity or widen the light emitting wavelength region.

The fluorescent light emitting material and the phosphorescent light emitting material which can be used in the organic electroluminescent element of the present invention are described in detail in, for example, paragraph Nos. [0100] to [0164] of JP-A-2008-270736 and paragraph Nos. [0088] to [0090] of JP-A-2007-266458, and the detailed descriptions in these publications can be applied to the present invention.

Examples of the phosphorescent light emitting material which can be used in the present invention include phosphorescent light emitting compounds or the like described in patent documents, for example, U.S. Pat. Nos. 6,303,238 and 6,097,147, WO00/57676, WO00/70655, WO01/08230, WO01/39234, WO01/41512, WO02/02714, WO02/15645, WO02/44189, WO05/19373, JP-A-2001-247859, JP-A-2002-302671, JP-A-2002-117978, JP-A-2003-133074, JP-A-2002-235076, JP-A-2003-123982, JP-A-2002-170684, EP1211257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635, and JP-A-2007-96259. Above all, examples of the light emitting material which is more preferred include phosphorescent light emitting metal complex compounds such as Ir complexes, Pt complexes, Cu complexes, Re complexes, W complexes, Rh complexes, Ru complexes, Pd complexes, Os complexes, Eu complexes, Tb complexes, Gd complexes, Dy complexes, and Ce complexes, and Ir complexes, Pt complexes, and Re complexes are particularly preferred. Above all, Ir complexes, Pt complexes, and Re complexes each including at least one coordination mode of a metal-carbon bond, a metal-nitrogen bond, a metal-oxygen bond, and a metal-sulfur bond are preferred. In addition, from the viewpoints of luminous efficiency, driving durability, chromaticity, or the like, Ir complexes and Pt complexes are particularly preferred, and Pt complexes are the most preferred.

The kind of the fluorescent light emitting material which can be used in the present invention is not particularly limited, but examples of the fluorescent light emitting material include benzoxazole, benzimidazole, benzothiazole, styrylbenzene, polyphenyl, diphenylbutadiene, tetraphenylbutadiene, naphthalimide, coumarin, pyrane, perinone, oxadiazole, aldazine, pyralizine, cyclopentadiene, bisstyrylanthracene, quinacridone, pyrrolopyridine, thiadiazolopyridine, cyclopentadiene, styrylamine, aromatic fused polycyclic compounds (anthracene, phenanthroline, pyrene, perylene, rubrene, pentacene, and the like), a variety of metal complexes typified by metal complexes of 8-quinolinol, pyrromethene complexes, and rare-earth complexes, polymer compounds such as polythiophene, polyphenylene, and polyphenylenevinylene, organic silanes, and derivatives thereof.

In addition, the compound described in paragraph No. [0082] of JP-A-2010-111620 can also be used as a light emitting material.

The light emitting layer in the organic electroluminescent element of the present invention is constituted as a mixed layer of a host material and a light emitting material.

The host material represented by the general formula (H-1) which can be used in the light emitting layer in the organic electroluminescent element of the present invention may be a hole transporting host material or an electron transporting property host material, but the host material is preferably a charge transporting material. The host material may be made of one kind or two or more kinds thereof. Examples thereof include a configuration in which an electron transporting host material and a hole transporting host material are mixed. Further, the light emitting layer may include a material which does not have a charge transporting property and does not emit light.

In addition, the light emitting layer may be made of a single layer or multiple layers of two or more layers. Each of the layers may include the same light emitting material or host material, and may also include a different material in every layer. In the case where a plurality of light emitting layers are present, each of the light emitting layers may emit light in a different luminous color from each other.

(Host Material)

The host material is a compound that usually plays a role in injecting or transporting charges in the light emitting layer and is also a compound which does not substantially emit light in itself. As used herein, the statement "which does not substantially emit light" means that the amount of light emission from the compound which does not substantially emit light is preferably 5% or less, more preferably 3% or less, and still more preferably 1% or less, with respect to the total amount of light emission in the entirety of the element.

The organic electroluminescent element of the present invention includes the host material represented by the general formula (H-1), but it may include other host materials. Examples of other host materials which can be used in the present invention include the following compounds:

conductive high-molecular oligomers such as pyrrole, indole, carbazole, azaindole, azacarbazole, triazole, oxazole, oxadiazole, pyrazole, imidazole, thiophene, benzothiophene, dibenzothiophene, furan, benzofuran, dibenzofuran, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, styrylamine compounds, porphyrin-based compounds, aromatic hydrocarbon compounds with fused rings (fluorene, naphthalene, phenanthrene, triphenylene, and the like), polysilane-based compounds, poly (N-vinylcarbazole), aniline-based copolymers, thiophene oligomers, and polythiophene, organic silanes, carbon films, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic anhydrides such as naphthalene perylene, a variety of metal complexes typified by metal complexes of phthalocyanine and 8-quinolinol derivatives and metal complexes having metal phthalocyanine, benzoxazole, or benzothiazole as a ligand thereof, and derivatives thereof (which may have a substituent or a fused ring). In addition, the compounds described in paragraph No. [0081] or [0083] of JP-A-2010-111620 can also be used.

The $T_1$ energy in the film state of the compound represented by the general formula (H-1) is preferably from 1.77 eV (40 kcal/mol) to 3.51 eV (81 kcal/mol), and more preferably from 2.39 eV (55 kcal/mol) to 3.25 eV (75 kcal/mol).

In the light emitting layer, the triplet lowest excited energy ($T_1$ energy) in the film state of the host material represented by the general formula (H-1) is preferably higher than the $T_1$ energy of the light emitting material represented by the general formula (1) from the viewpoints of color purity, luminous efficiency, and driving durability. The $T_1$ of the host material is preferably higher than the $S_1$ of the light emitting material by 0.1 eV or more, more preferably by 0.2 eV or more, and still more preferably by 0.3 eV or more.

When the $T_1$ in the film state of the host material is lower than the $T_1$ of the light emitting material, the light emission is lost, and thus, the host material is required to have a higher $T_1$ than the $T_1$ of the light emitting material. Further, even in the case where the $T_1$ of the host material is higher than the $T_1$ of the light emitting material, a small difference in the $T_1$ of the both leads to partial reverse energy movement from the emitting material to the host material, which causes reduction in efficiency, reduction in color purity, and reduction in durability. Therefore, there is a demand for a host material having a sufficiently high $T_1$, and high chemical stability and carrier injecting/transporting properties.

In particular, in the case where the luminous color from the organic electroluminescent element is green (the light emission peak wavelength is from 490 nm to 580 nm), from the viewpoint of luminous efficiency, the $T_1$ energy is more preferably from 2.39 eV (55 kcal/mol) to 2.82 eV (65 kcal/mol).

By measuring the phosphorescent luminous spectrum of a thin film of the material, the $T_1$ energy can be found from the short-wavelength end thereof. For instance, a film of the material is formed in a thickness of about 50 nm by a vacuum deposition method over a washed quartz glass substrate, and the phosphorescent luminous spectrum of the thin film is measured using an F-7000 Hitachi spectrofluorophotometer (Hitachi High-Technologies Corporation) at the temperature of liquid nitrogen. The $T_1$ energy can be determined by converting a rising wavelength on the short-wavelength side of the luminous spectrum thus obtained to energy units.

(Other Layers)

The organic electroluminescent element of the present invention may include layers other than the light emitting layer.

Examples of the organic layer other than the light emitting layer which the organic layer(s) may have include a hole injecting layer (which may also be referred to as a charge generating layer), a hole transporting layer, a blocking layer (a hole blocking layer, an exciton blocking layer, and the like), and an electron transporting layer. Specifically, examples of the layer configuration include those described below, but it should not be construed that the present invention is limited to these configurations.

Anode/hole transporting layer/light emitting layer/electron transporting layer/cathode, Anode/hole transporting layer/light emitting layer/blocking layer/electron transporting layer/cathode, Anode/hole transporting layer/light emitting layer/blocking layer/electron transporting layer/electron injecting layer/cathode, Anode/hole injecting layer/hole transporting layer/light emitting layer/blocking layer/electron transporting layer/cathode, Anode/hole injecting layer/hole transporting layer/light emitting layer/electron transporting layer/electron injecting layer/cathode, Anode/hole injecting layer/hole transporting layer/light emitting layer/blocking layer/electron transporting layer/electron injecting layer/cathode, and Anode/hole injecting layer/hole transporting layer/blocking layer/light emitting layer/blocking layer/electron transporting layer/electron injecting layer/cathode.

The organic electroluminescent element of the present invention preferably includes at least one (A) organic layer which is preferably disposed between the anode and the light emitting layer. Examples of the (A) organic layer which is preferably disposed between the anode and the light emitting layer include an hole injecting layer, a hole transporting layer, and an electron blocking layer from the anode side.

The organic electroluminescent element of the present invention preferably includes at least one (B) organic layer which is preferably disposed between the cathode and the light emitting layer. Examples of the (B) organic layer which is preferably disposed between the cathode and the light emitting layer include an electron injecting layer, an electron transporting layer, and a hole blocking layer from the cathode side.

Specifically, an example of the preferred aspects of the organic electroluminescent element of the present invention is the aspect shown in FIG. 1, in which a hole injecting layer 4, a hole transporting layer 5, a light emitting layer 6, a hole blocking layer 7, and an electron transporting layer 8 are laminated in this order as the organic layer from the anode 3 side.

Hereinafter, the layers other than the light emitting layer which the organic electroluminescent element of the present invention may have will be described.

(A) Organic Layer Preferably Disposed Between Anode and Light Emitting Layer:

First, the (A) organic layer preferably disposed between the Anode and the Light Emitting Layer Will be Described.

(A-1) Hole Injecting Layer and Hole Transporting Layer

The hole injecting layer and the hole transporting layer are layers having a function of receiving holes from the anode or the anode side and transporting them to the cathode side.

In the present invention, preferred examples of the hole transporting material which is used in the hole transporting layer include a triarylamine compound represented by the following general formula (HT-1).

[Chem. 25]

General Formula (HT-1)

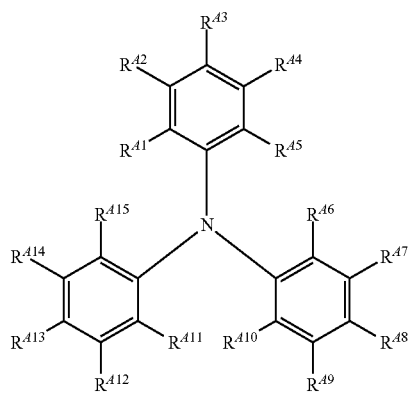

(In the general formula (HT-1), $R^{41}$ to $R^{415}$ each independently represent a hydrogen atom or a substituent.)

Examples of the substituents represented by $R^{41}$ to $R^{415}$ include the substituents exemplified in the Substituent Group A, and the adjacent substituents may be bonded to each other via a single bond or a linking group to form a ring. From the viewpoint of heat resistance and durability, at least one of $R^{41}$ to $R^{45}$ and at least one of $R^{46}$ to $R^{410}$ are each preferably an aryl group.

Specific examples of the compound represented by the general formula (HT-1) are shown below, but the present invention is not limited thereto.

[Chem. 26]

(HTL-1)

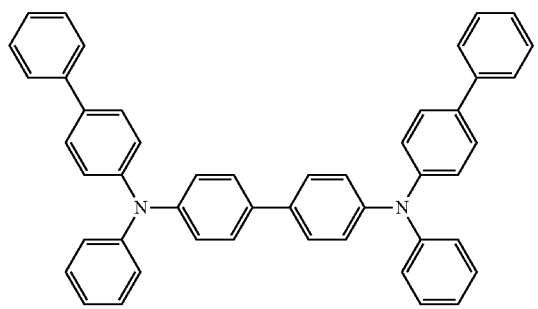

(HTL-2)

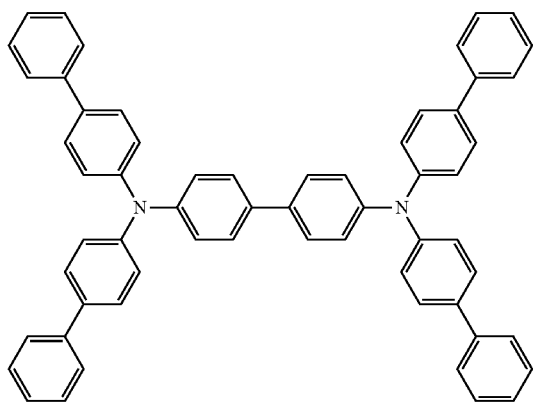

(HTL-3)

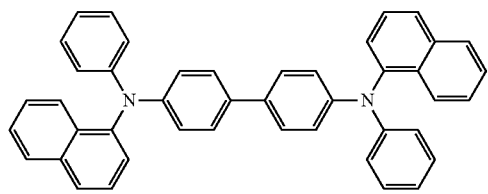

(HTL-4)

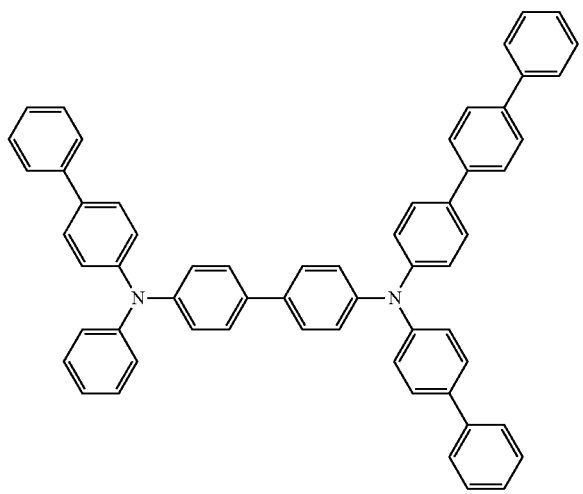

-continued
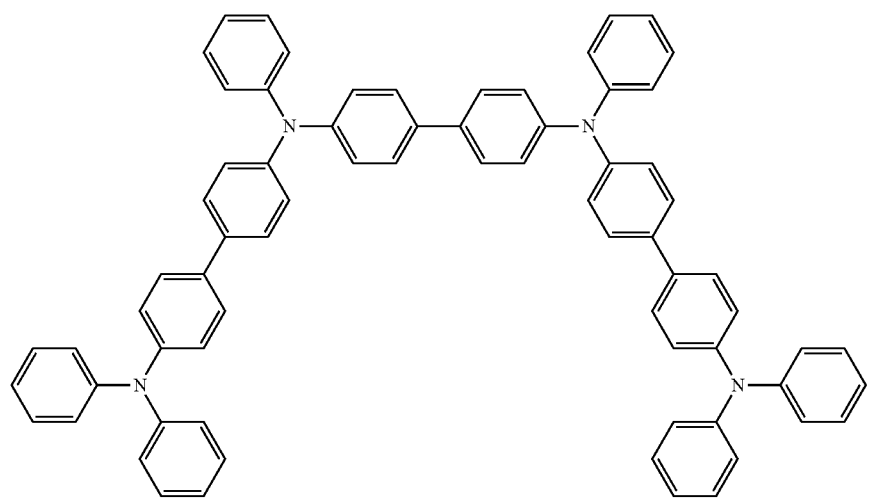
(HTL-5)
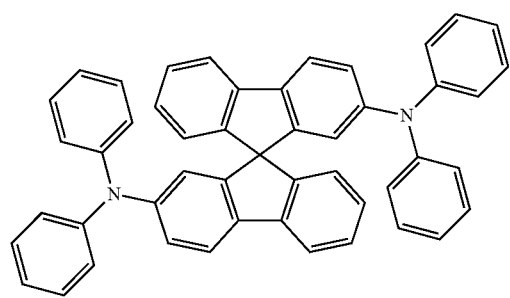
(HTL-6)
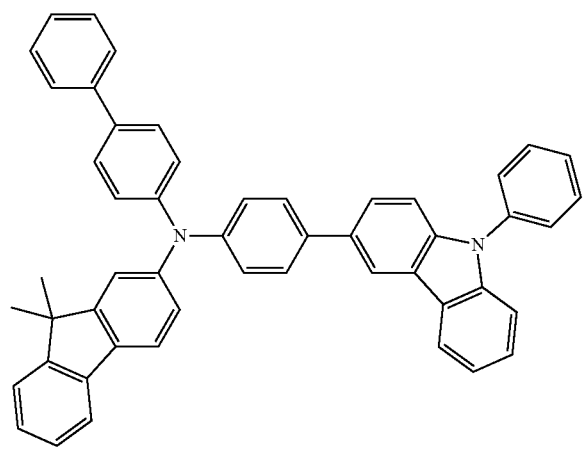
(HTL-7)
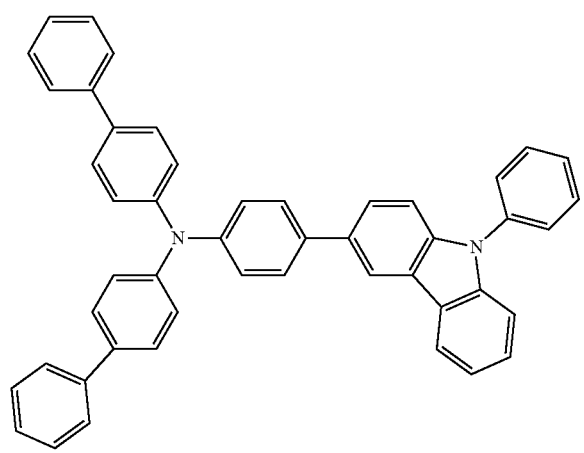
(HTL-8)

[Chem. 27]

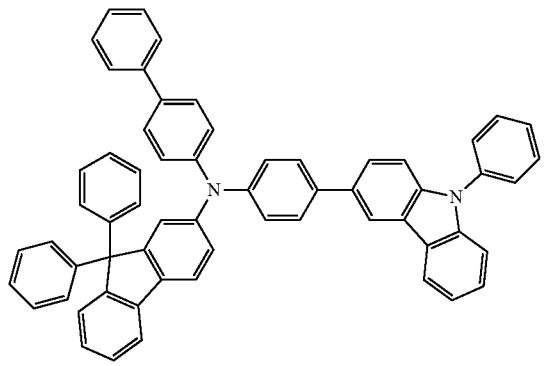
(HTL-9)

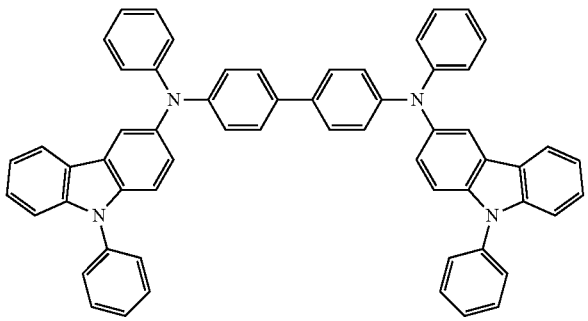
(HTL-10)

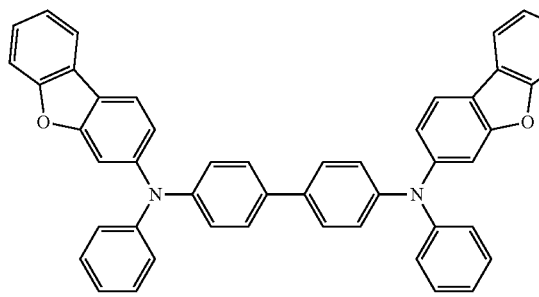
(HTL-11)

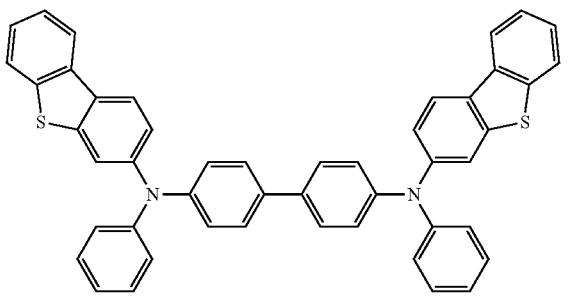
(HTL-12)

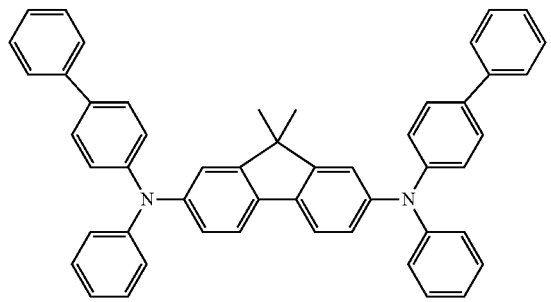
(HTL-13)

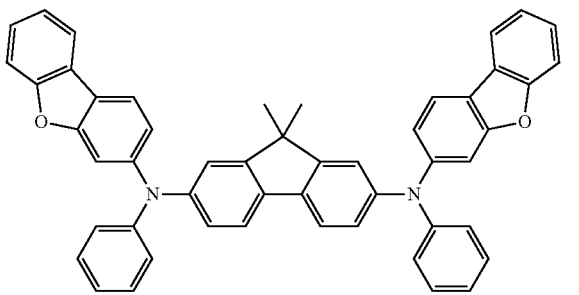
(HTL-14)

In addition, with respect to the hole injecting layer and the hole transporting layer, the detailed descriptions in paragraph Nos. [0165] to [0167] of JP-A-2008-270736 can be applied to the present invention. Further, the detailed descriptions in paragraph Nos. [0250] to [0339] of JP-A-2011-71452 can be applied to the hole injecting layer and the hole transporting layer of the present invention.

The hole injecting layer preferably contains an electron receiving dopant. By incorporating the electron receiving dopant in the hole injecting layer, there are effects in which, for example, the hole injecting properties are improved, the driving voltage is lowered, and the efficiency is enhanced. The electron receiving dopant may be any one of organic materials and inorganic materials as long as it is capable of withdrawing electrons from a material to be doped and generating radical cations, and examples thereof include TCNQ compounds such as tetracyanoquinodimethane (TCNQ) and tetrafluorotetracyanoquinodimethane ($F_4$-TCNQ), hexaazatriphenylene compounds such as hexacyanohexaazatriphenylene (HAT-CN), and molybdenum oxide.

The electron receiving dopant in the hole injecting layer is contained in the amount of preferably from 0.01% by mass to 50% by mass, more preferably from 0.1% by mass to 40% by mass, and still more preferably from 0.2% by mass to 30% by mass, with respect to the total mass of the compounds forming the hole injecting layer.

(A-2) Electron Blocking Layer

The electron blocking layer is a layer having a function of preventing the electrons, which have been transported from the cathode side to the light emitting layer, from passing through to the anode side. In the present invention, the electron blocking layer can be provided as an organic layer adjacent to the light emitting layer and the anode side.

As the organic compound constituting the electron blocking layer, for example, those exemplified above as the hole transporting material can be applied.

The thickness of the electron blocking layer is preferably from 1 nm to 500 nm, more preferably from 3 nm to 100 nm, and still more preferably from 5 nm to 50 nm.

The electron blocking layer may have either a single layer structure composed of one kind or two or more kinds of the above-described materials or a multilayer structure composed of a plurality of layers having the same composition or different compositions.

The material used in the electron blocking layer preferably has higher $S_1$ energy than that of the light emitting material from the viewpoints of color purity, luminous efficiency, and driving durability. The $S_1$ in the film state of the material used in the electron blocking layer is higher than the $S_1$ of the light emitting material preferably by 0.1 eV or more, more preferably by 0.2 eV or more, and still more preferably by 0.3 eV or more.

(B) Organic Layer Preferably Disposed Between Cathode and Light Emitting Layer

Next, the (B) organic layer preferably disposed between the cathode and the light emitting layer will be described.

(B-1) Electron Injecting Layer and Electron Transporting Layer

The electron injecting layer and the electron transporting layer are layers having a function of receiving electrons from the cathode or the cathode side and transporting them to the anode side. The electron injecting material and the electron transporting material used in these layers may be either a low-molecular compound or a high-molecular compound.

As the electron transporting material, anyone selected from aromatic ring tetracarboxylic acid anhydrides, such as pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, benzimidazole derivatives, imidazopyridine derivatives, fluorenone derivatives, anthraquinodimethane derivatives, anthrone derivatives, diphenylquinone derivatives, thiopyranedioxide derivatives, carbodiimide derivatives, fluorenylidenemethane derivatives, distyrylpyrazine derivatives, naphthalene, and perylene; various metal complexes typified by metal complexes of phthalocyanine derivatives or 8-quinolinol derivatives and metal complexes having metal phthalocyanine, benzoxazole, or benzothiazole as a ligand thereof; organic silane derivatives typified by silole; and hydrocarbon compounds with fused rings, such as naphthalene, anthracene, phenanthrene, triphenylene, and pyrene is preferred, and any one selected from pyridine derivatives, benzimidazole derivatives, imidazopyridine derivatives, metal complexes, and hydrocarbon compounds with fused rings is more preferred.

From the viewpoint of decreasing the driving voltage, the thickness of each of the electron injecting layer and the electron transporting layer is preferably 500 nm or less.

The thickness of the electron transporting layer is preferably from 1 nm to 500 nm, more preferably from 5 nm to 200 nm, and still more preferably from 10 nm to 100 nm. In addition, the thickness of the electron injecting layer is preferably from 0.1 nm to 200 nm, more preferably from 0.2 nm to 100 nm, and still more preferably from 0.5 nm to 50 nm.

The electron injecting layer and the electron transporting layer may have either a single layer structure composed of one kind or two or more kinds of the above-described materials or a multilayer structure composed of a plurality of layers having the same composition or different compositions.

The electron injecting layer preferably contains an electron donating dopant. By incorporating the electron donating dopant in the electron injecting layer, there are effects that, for example, the electron injecting properties are improved, the driving voltage is lowered, and the efficiency is improved. The electron donating dopant may be any one of organic materials and inorganic materials as long as it is capable of giving electrons to the material to be doped and generating radical anions, and examples thereof include dihydroimidazole compounds such as tetrathiafulvalene (TTF), tetrathianaphthacene (TTT), and bis-[1,3-diethyl-2-methyl-1,2-dihydrobenzimidazolyl], lithium, and cesium.

The electron donating dopant in the electron injecting layer is contained in the amount of preferably from 0.01% by mass to 50% by mass, more preferably from 0.1% by mass to 40% by mass, and still more preferably 0.5% by mass to 30% by mass, with respect to the total mass of the compounds forming the electron injecting layer.

(B-2) Hole Blocking Layer

The hole blocking layer is a layer having a function of preventing holes, which have been transported from the anode side to the light emitting layer, from passing through to the cathode side. In the present invention, the hole blocking layer can be provided as an organic layer adjacent to the light emitting layer on the cathode side.

In order that the $S_1$ energy of the organic compound in the film state constituting the hole blocking layer prevents the energy movement of excitons produced in the light emitting layer, and thus, does not lower the luminous efficiency, it is preferably higher than $S_1$ energy of the light emitting material.

Examples of the organic compounds constituting the hole blocking layer include aluminum complexes such as aluminum (III) bis(2-methyl-8-quinolinato)-4-phenylphenolate (abbreviated as Balq), triazole derivatives, and phenanthroline derivatives such as 2,9-dimethyl-4,7-diphenyl-1,10-phenanthroline (abbreviated as BCP).

The thickness of the hole blocking layer is preferably from 1 nm to 500 nm, more preferably from 3 nm to 100 nm, and still more preferably from 5 nm to 50 nm.

The hole blocking layer may have either a single layer structure composed of one kind or two or more kinds of the above-described materials or a multilayer structure composed of a plurality of layers having the same composition or different compositions.

The material used in the hole blocking layer preferably has higher $S_1$ energy than that of the light emitting material from the viewpoints of color purity, luminous efficiency, and driving durability. The $S_1$ in the film state of the material used in the hole blocking layer is higher than the $S_1$ of the light emitting material preferably by 0.1 eV or more, more preferably by 0.2 eV or more, and still more preferably by 0.3 eV or more.

(B-3) Material which is Particularly Preferably Used in Organic Layer, Preferably Disposed Between Cathode and Light Emitting Layer For the organic electroluminescent element of the present invention, at least one layer of the (B) organic layer (s) which is preferably disposed between the cathode and the light emitting layer is preferably included between the light emitting layer and the cathode, and the organic layer(s) preferably contains at least one kind of compound represented by the following general formula (O-1) from the viewpoints of the efficiency and the driving voltage of the element. Hereinafter, the general formula (O-1) will be described.

[Chem. 28]

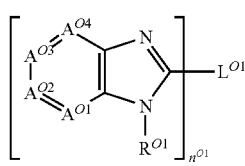

(O-1)

(In the general formula (O-1), $R^{O1}$ represents an alkyl group, an aryl group, or a heteroaryl group. $A^{O1}$ to $A^{O4}$ each independently represent C—$R^4$ or a nitrogen atom. $R^4$ represents a hydrogen atom, an alkyl group, an aryl group, or a heteroaryl group, and a plurality of $R^4$s may be the same as or different from each other. $L^{O1}$ represents any of divalent to hexavalent linking groups with an aryl ring or a heteroaryl ring. not represents an integer of 2 to 6).

$R^{O1}$ represents an alkyl group (preferably having 1 to 8 carbon atoms), an aryl group (preferably having 6 to 30 carbon atoms), or a heteroaryl group (preferably having 4 to 12 carbon atoms), which may have a substituent selected from the Substituent Group A as described above. $R^{O1}$ is preferably an aryl group or a heteroaryl group, and more preferably an aryl group. Preferred examples of the substituent in the case where the aryl group of $R^{O1}$ has a substituent include an alkyl group, an aryl group, and a cyano group, more preferred examples thereof include an alkyl group and an aryl group, and still more preferred examples thereof include an aryl group. In the case where the aryl group of $R^{O1}$ has a plurality of substituents, the plurality of substituents may be bonded to each other to form a 5- or 6-membered ring. The aryl group of $R^{O1}$ is preferably a phenyl group which may have a substituent selected from the Substituent Group A, more preferably a phenyl group which may be substituted with an alkyl group or an aryl group, and still more preferably an unsubstituted phenyl group or 2-phenylphenyl group.

$A^{O1}$ to $A^{O4}$ each independently represent C—$R^4$ or a nitrogen atom. It is preferable that 0 to 2 groups out of $A^{O1}$ to $A^{O4}$ be nitrogen atoms; and it is more preferable that 0 or 1 group out of $A^{O1}$ to $A^{O4}$ be nitrogen atoms. It is preferable that all of $A^{O1}$ to $A^{O4}$ be C—$R^4$, or $A^{O1}$ be a nitrogen atom, and $A^{O2}$ to $A^{O4}$ be C—$R^4$; it is more preferable that $A^{O1}$ be a nitrogen atom, and $A^{O2}$ to $A^{O4}$ be C—$R^4$; it is still more preferable that $A^{O1}$ be a nitrogen atom, $A^{O2}$ to $A^{O4}$ be C—$R^4$, and $R^4$s be all hydrogen atoms.

$R^4$ represents a hydrogen atom, an alkyl group (preferably having 1 to 8 carbon atoms), an aryl group (preferably having 6 to 30 carbon atoms), or a heteroaryl group (preferably having 4 to 12 carbon atoms), which may have a substituent selected from the Substituent Group A as described above. Further, a plurality of $R^4$s may be the same as or different from each other. $R^4$ is preferably a hydrogen atom or an alkyl group, and more preferably a hydrogen atom.

$L^{O1}$ represents any of divalent to hexavalent linking groups including an aryl ring (preferably having 6 to 30 carbon atoms) or a heteroaryl ring (preferably having 4 to 12 carbon atoms). $L^{O1}$ is preferably an arylene group, a heteroarylene group, an aryltriyl group, or a heteroaryltriyl group, more preferably a phenylene group, a biphenylene group, or a benzenetriyl group, and still more preferably a biphenylene group or a benzenetriyl group. $L^{O1}$ may have a substituent selected from the Substituent Group A as described above, and in a case of having the substituent, the substituent is preferably an alkyl group, an aryl group, or a cyano group. Specific examples of $L^{O1}$ include the following.

[Chem. 29]

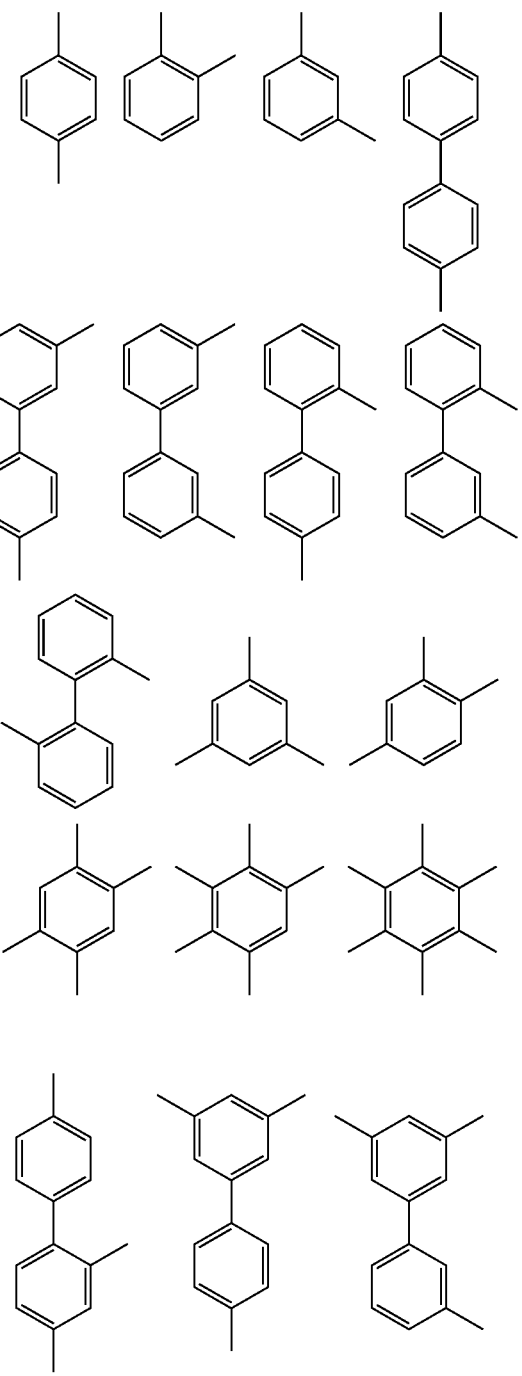

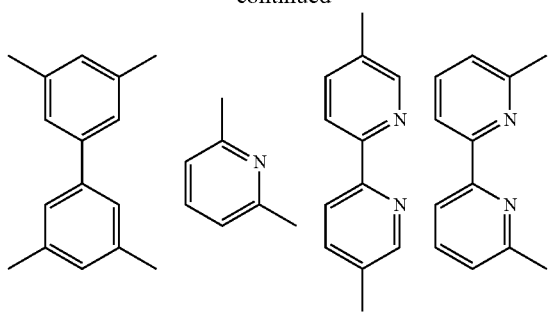
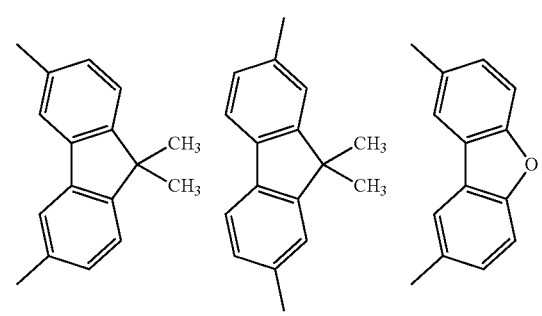
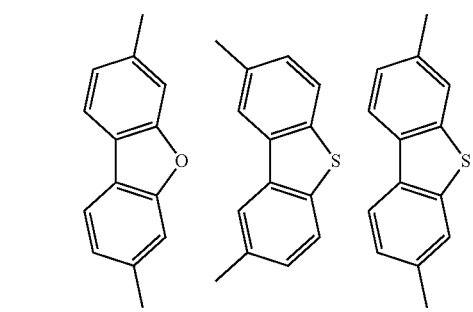
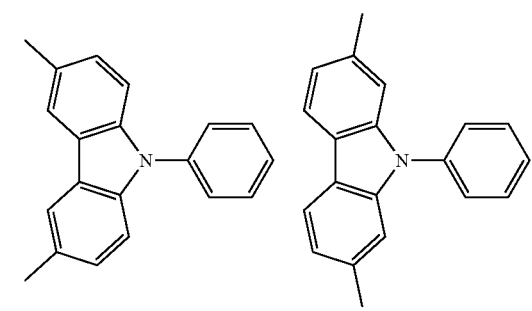

$n^{O1}$ represents an integer of 2 to 6, preferably an integer of 2 to 4, and more preferably 2 or 3. $n^{O1}$ is most preferably 3 from the viewpoint of the efficiency of an element, or most preferably 2 from the viewpoint of the durability of an element.

The compound represented by the general formula (O-1) is more preferably a compound represented by the following general formula (O-2).

[Chem. 30]

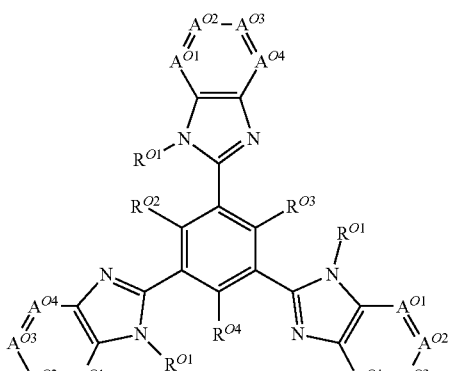

(O-2)

(In the general formula (O-2), $R^{O1}$ represents an alkyl group, an aryl group, or a heteroaryl group. $R^{O2}$ to $R^{O4}$ each independently represent a hydrogen atom, an alkyl group, an aryl group, or a heteroaryl group. $A^{O1}$ to $A^{O4}$ each independently represent C—$R^A$ or a nitrogen atom. $R^A$ represents a hydrogen atom, an alkyl group, an aryl group, or a heteroaryl group, and a plurality of $R^A$s may be the same as or different from each other.)

$R^{O1}$ and $A^{O1}$ to $A^{O4}$ have the same definitions as $R^{O1}$ and $A^{O1}$ to $A^{O4}$ in the general formula (O-1), and the preferred ranges thereof are also the same.

$R^{O2}$ to $R^{O4}$ each independently represent a hydrogen atom, an alkyl group (preferably having 1 to 8 carbon atoms), an aryl group (preferably having 6 to 30 carbon atoms), or a heteroaryl group (preferably having 4 to 12 carbon atoms), and these groups may have a substituent selected from the Substituent Group A as described above. $R^{O2}$ to $R^{O4}$ are preferably a hydrogen atom, an alkyl group, or an aryl group, more preferably a hydrogen atom or an aryl group, and most preferably a hydrogen atom.

The glass transition temperature (Tg) of the compound represented by the general formula (O-1) is preferably from 100° C. to 300° C., more preferably from 120° C. to 300° C., still more preferably from 120° C. to 300° C., further more preferably from 140° C. to 300° C., from the viewpoint of stability at the time of storage at a high temperature, or stable operation against heat generation during driving while driving at a high temperature.

Specific examples of the compound represented by the general formula (O-1) will be shown below, but the present invention is not limited thereto.

[Chem. 31]
OM-1
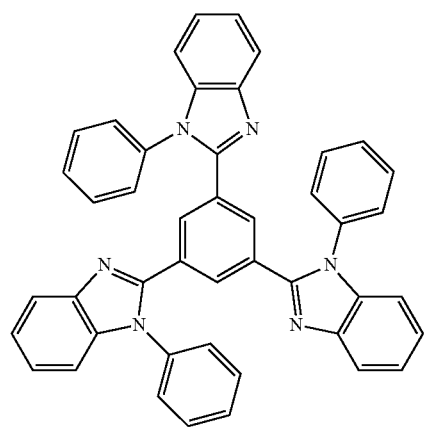
OM-2
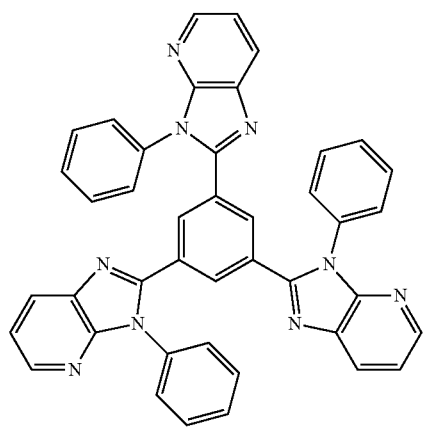
OM-3
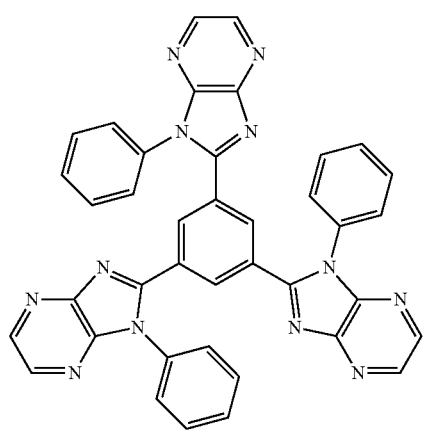
OM-4
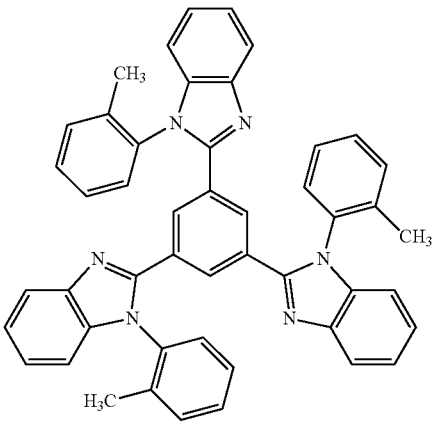
OM-5
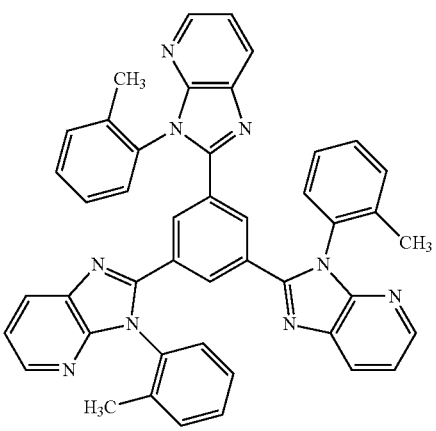
OM-6
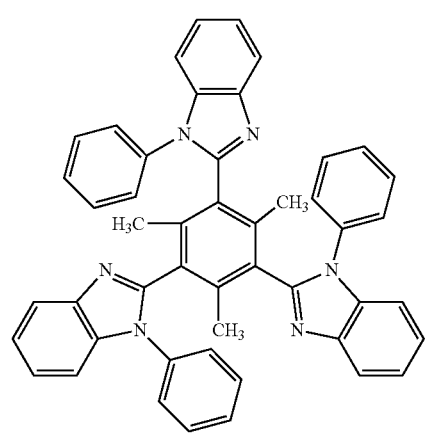

-continued
[Chem. 32]
OM-7
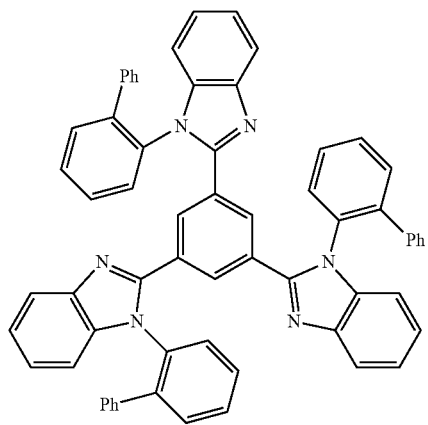
OM-10
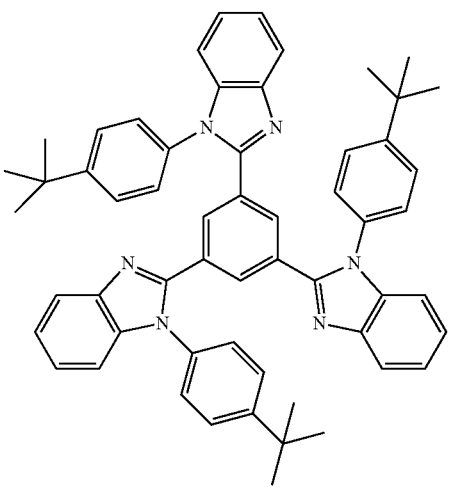
OM-8
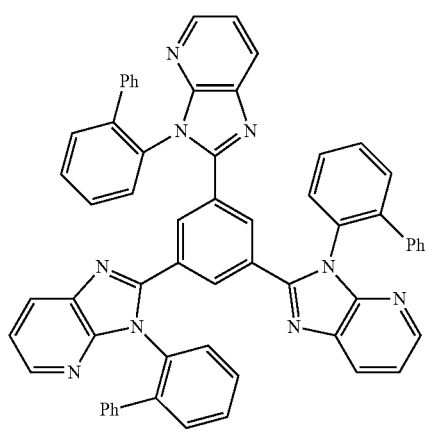
OM-11
OM-9
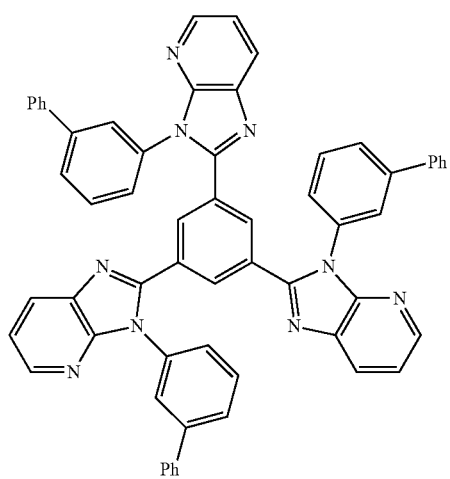
OM-12

OM-13

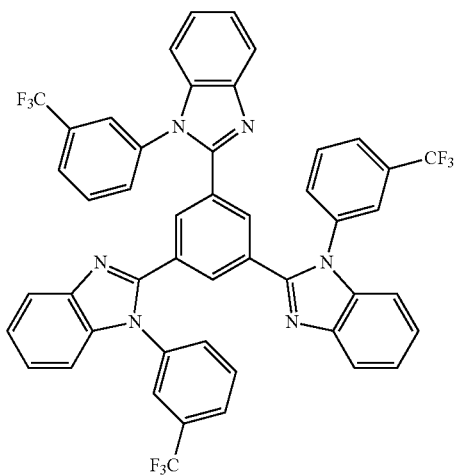

OM-14

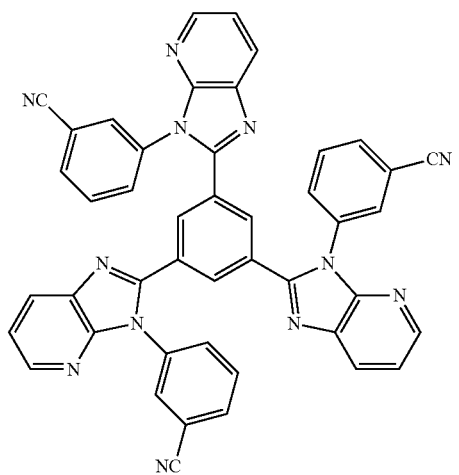

OM-15

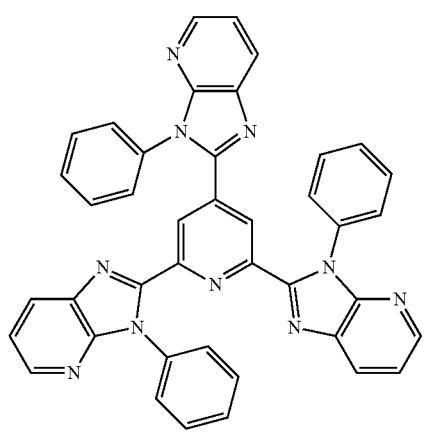

OM-16

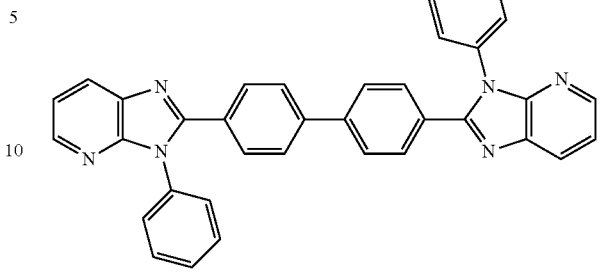

OM-17

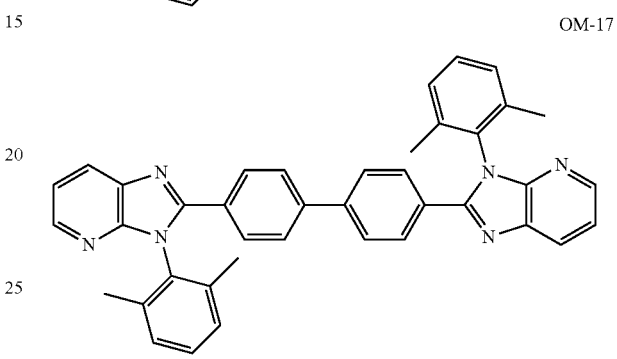

OM-18

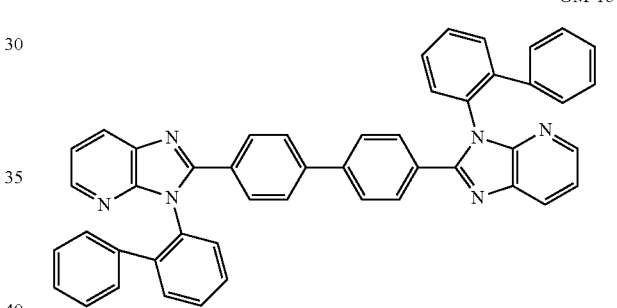

The compound represented by the general formula (O-1) can be synthesized by the method described in JP-A-2001-335776. After the synthesis, the product is preferably purified by column chromatography, recrystallization, reprecipitation, or the like, and then purified by sublimation purification. By sublimation purification, it is possible not only to separate organic impurities but also to effectively remove inorganic salts, residual solvent, moisture, or the like.

In the light emitting element of the present invention, the compound represented by the general formula (O-1) is contained in an organic layer between the light emitting layer and the cathode, and more preferably contained in a layer on the cathode side adjacent to the light emitting layer.

The compound represented by the general formula (O-1) is contained in the amount of preferably from 70% by mass to 100% by mass, and more preferably from 85% by mass to 100% by mass, with respect to the total mass of the organic layer added.

Preferred examples of other materials used in the electron injecting layer or the electron transporting layer in the organic electroluminescent element of the present invention include silole compounds described in JP-A-9-194487 or the like, phosphine oxide compounds described in JP-A-2006-73581 or the like, nitrogen-containing aromatic 6-membered ring hetero compounds described in JP-A-2005-276801, JP-A-2006-225320, WO2005/085387, or the like, compounds having nitrogen-containing aromatic 6-membered hetero structures and carbazole structures, described in WO2003/080760, WO2005/085387, or the like, and aromatic hydrocarbon compounds described in US2009/0009065, WO2010/134350, JP-T-2010-535806, or the like (naphthalene compounds, anthracene compounds, triphenylene compounds, phenanthrene compounds, pyrene compounds, fluoranthene compounds, and the like).

<Protective Layer>

In the present invention, the entirety of the organic electroluminescent element may be protected by a protective layer.

For the protective layer, the detailed descriptions in paragraph Nos. [0169] to [0170] of JP-A-2008-270736 can also be applied to the present invention. Incidentally, the materials for the protective layer may be either an inorganic material or an organic material.

<Sealing Enclosure>

For the organic electroluminescent element according to the present invention, the entirety of the element may be sealed using a sealing enclosure.

For the sealing enclosure, the detailed description in paragraph No. [0171] of JP-A-2008-270736 can be applied to the present invention.

<Driving Method>

The organic electroluminescent element of the present invention can emit light by applying a direct current (it may contain an alternate current component, if necessary) voltage (typically from 2 volts to 15 volts) or a direct current between the anode and the cathode.

As a driving method of the organic electroluminescent element of the present invention, driving methods described in each of the publications of JP-A-2-148687, JP-A-6-301355, JP-A-5-29080, JP-A-7-134558, JP-A-8-234685, and JP-A-8-241047, Japanese Patent No. 2784615, and U.S. Pat. Nos. 5,828,429 and 6,023,308 can be applied.

The external quantum efficiency of the organic electroluminescent element of the present invention is preferably 5% or more, more preferably 6% or more, and still more preferably 7% or more. As to the numerical value of the external quantum efficiency, a maximum value of the external quantum efficiency obtained when the element is driven at 20° C., or a value of the external quantum efficiency in the vicinity of from 300 cd/m$^2$ to 400 cd/m$^2$ obtained when the element is driven at 20° C. can be employed.

The internal quantum efficiency of the organic electroluminescent element of the present invention is preferably 30% or more, more preferably 50% or more, and still more preferably 70% or more. The internal quantum efficiency of the element is calculated by dividing the external quantum efficiency by a light extraction efficiency. The light extraction efficiency in usual organic EL elements is about 20%, but in consideration of the shape of a substrate, the shape of an electrode, the film thickness of an organic layer, the film thickness of an inorganic layer, the refractive index of an organic layer, the refractive index of an inorganic layer, or the like, it is possible to increase the light extraction efficiency to 20% or more.

<Light Emitting Wavelength>

In the organic electroluminescent element of the present invention, the light emitting wavelength is not limited, but is preferably used for green light emission. Above all, in the organic electroluminescent element of the present invention, the compound represented by the general formula (1) is preferably used as a phosphorescent light emitting material to emit light, and particularly preferably to emit green phosphorescent light.

The maximum light emitting wavelength of the organic electroluminescent element of the present invention is preferably 495 nm or more and less than 560 nm, more preferably 500 nm or more and less than 550, and particularly preferably 505 nm or more and less than 540 nm.

<Use of Organic Electroluminescent Element of the Present Invention>

The organic electroluminescent element of the present invention can be suitably used for display elements, displays, backlights, electrophotography, illumination light sources, recording light sources, exposure light sources, readout light sources, signs, billboards, interior decorations, optical communications, and the like, and particularly preferably for devices driven in a region of high-intensity luminescence, such as a light emitting device, an illumination device, and a display device.

[Light Emitting Device]

The light emitting device of the present invention may include the organic electroluminescent element of the present invention.

Next, the light emitting device of the present invention will be described with reference to FIG. 2.

The light emitting device of the present invention is formed by using the organic electroluminescent element.

Figure 2:
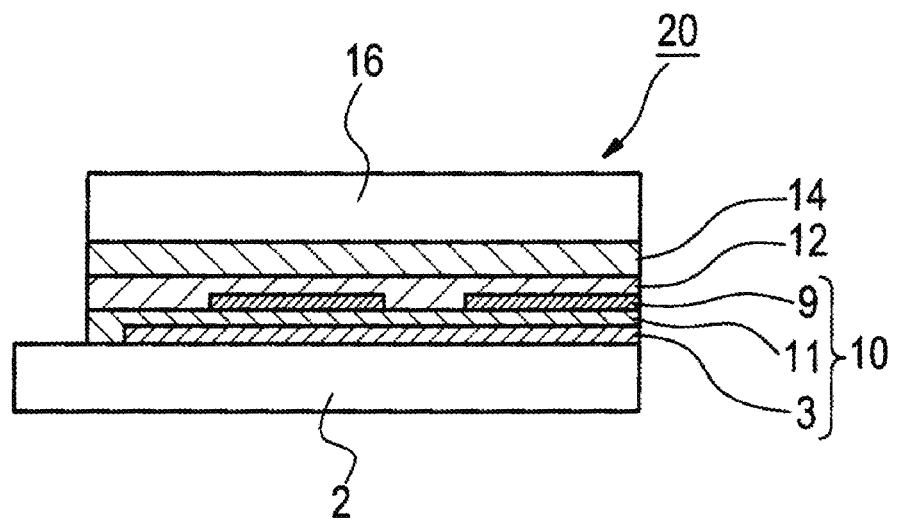
FIG. 2 is a schematic view showing one example of a light emitting device according to the present invention.

FIG. 2 is a cross-sectional view schematically showing one example of the light emitting device of the present invention. The light emitting device 20 in FIG. 2 is constituted with a transparent substrate 2 (supporting substrate), an organic electroluminescent element 10, a sealing enclosure 16, and the like.

The organic electroluminescent element 10 is formed by laminating on the substrate 2 an anode 3 (first electrode), an organic layer 11, and a cathode 9 (second electrode) in this order. In addition, a protective layer 12 is laminated on the cathode 9, and the sealing enclosure 16 is further provided via an adhesive layer 14 on the protective layer 12. Incidentally, a part of each of the electrodes 3 and 9, a diaphragm, an insulating layer, and the like are omitted.

Here, a photocurable adhesive such as an epoxy resin, or a thermosetting adhesive can be used for the adhesive layer 14, and for example, a thermosetting adhesive sheet may also be used.

The light emitting device of the present invention is not particularly limited in its use, and it can be used as not only an illumination device but also a display device of a television set, a personal computer, a mobile phone, electronic paper, or the like.

[Illumination Device]

The illumination device of the present invention includes the organic electroluminescent element of the present invention.

Next, the illumination device of the present invention will be described with reference to FIG. 3.

Figure 3:
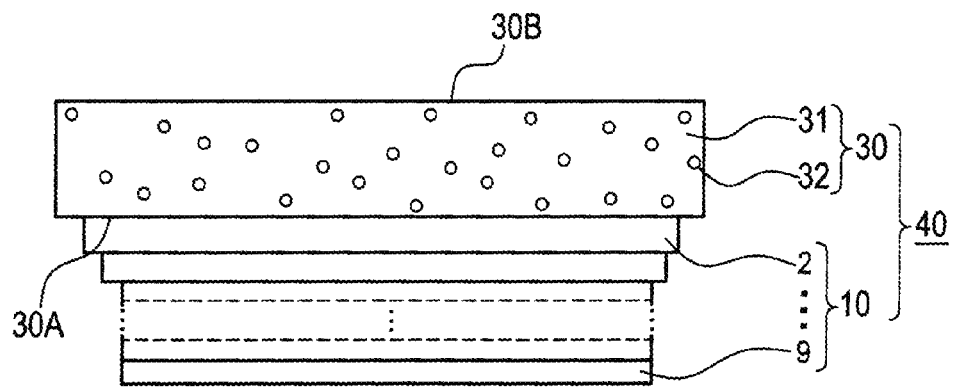
FIG. 3 is a schematic view showing one example of an illumination device according to the present invention.

FIG. 3 is a cross-sectional view schematically showing one example of the illumination device of the present invention. An illumination device 40 of the present invention includes, as shown in FIG. 3, the above-described organic EL element 10 and a light scattering member 30. More specifically, the illumination device 40 is configured such that the substrate 2 of the organic EL element 10 and the light scattering member 30 are in contact with each other.

The light scattering member 30 is not particularly limited as long as it can scatter light, but in FIG. 3, a member obtained by dispersing fine particles 32 in a transparent substrate 31 is used. Suitable examples of the transparent substrate 31 include a glass substrate, and suitable examples of the fine particles 32 include transparent resin fine particles. As the glass substrate and the transparent resin fine particles, a known product can be used for both. In such an illumination device 40, when light emitted from the organic electroluminescent element 10 is incident on a light incident surface 30A of the scattering member 30, the incident light is scattered by the light scattering member 30 and the scattered light is output as illuminating light from a light output surface 30B.

[Display Device]

The display device of the present invention may include the organic electroluminescent element of the present invention.

The display device of the present invention may be used for, for example, a display device of a television set, a personal computer, a mobile phone, electronic paper, or the like.

EXAMPLES

Hereinafter, the present invention will be described in more detail with reference to Examples and Comparative Examples. The materials, use amounts, ratios, treatment details, treatment procedures, and the like shown in the following Examples can be appropriately modified in so far as the gist of the present invention is not deviated. Accordingly, it is not construed that the scope of the present invention is limited to the specific examples shown below.

<Preparation of Materials>

(Synthesis of Light Emitting Materials)

The following light emitting materials (Pt-1) to (Pt-8) which are the compounds represented by the general formula (1) were synthesized according to Examples of JP-A-2005-310773.

Chem. 33

Light Emitting Materials

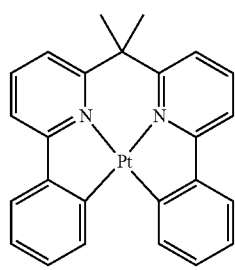
(Pt-1)

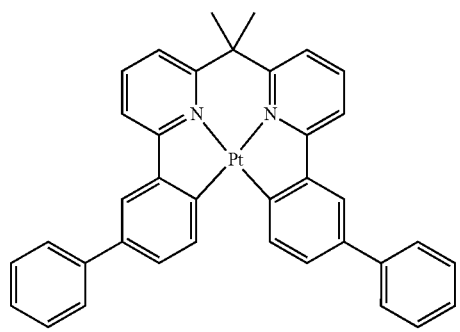
(Pt-2)

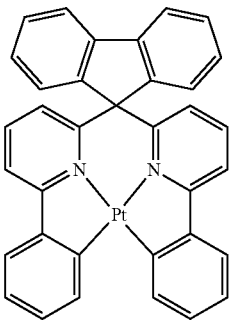
(Pt-3)

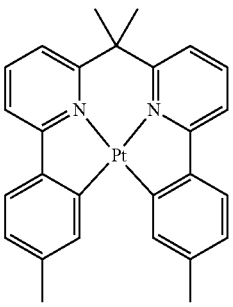
(Pt-4)

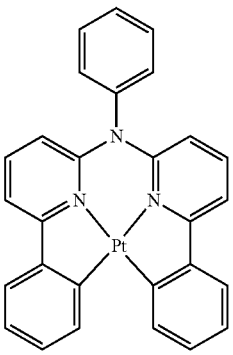
(Pt-5)

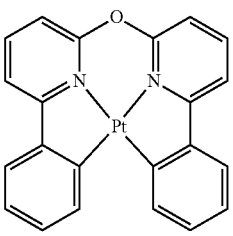
(Pt-6)

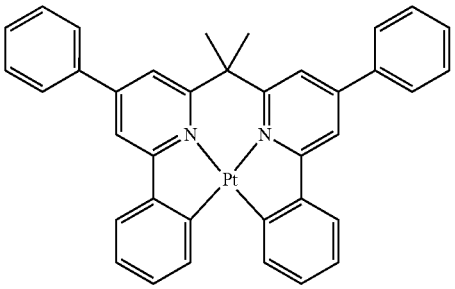
(Pt-7)

(Pt-8)
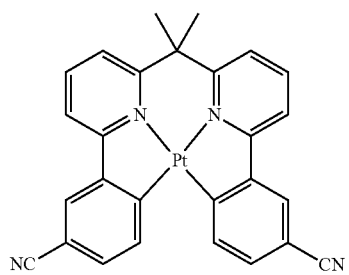
(Synthesis of Host Materials)
The following host materials (EH-1) to (EH-7) which are the compounds represented by the general formula (H-1) were synthesized according to JP-A-2011-91355, WO2008-056746, WO2007-063754, WO2010/131855, or the like.
[Chem. 34]
Host Compounds
(EH-1)
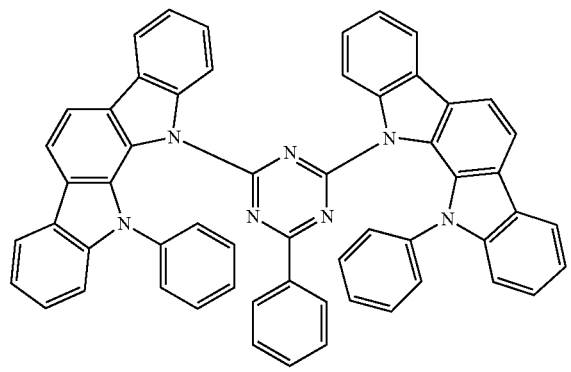
(EH-2)
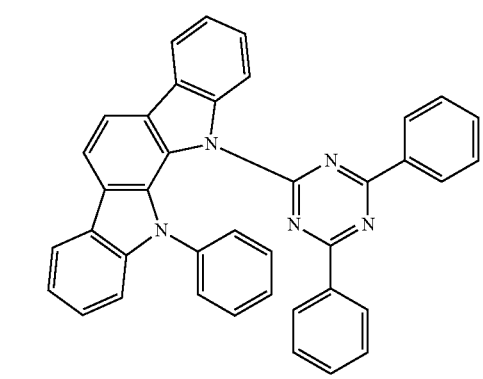
(EH-3)
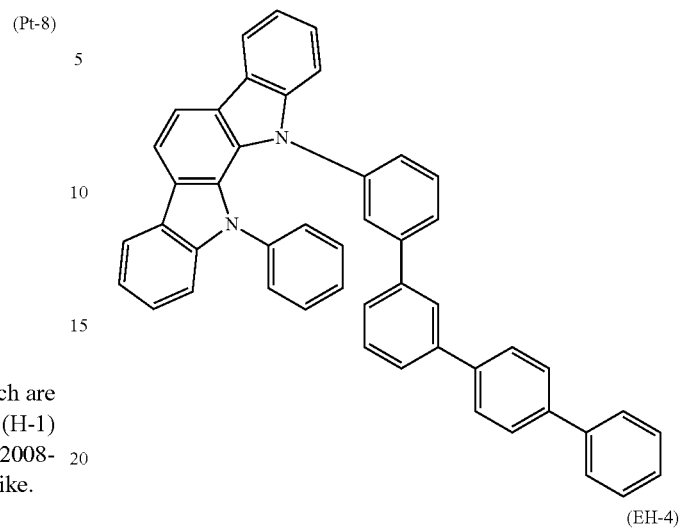
(EH-4)
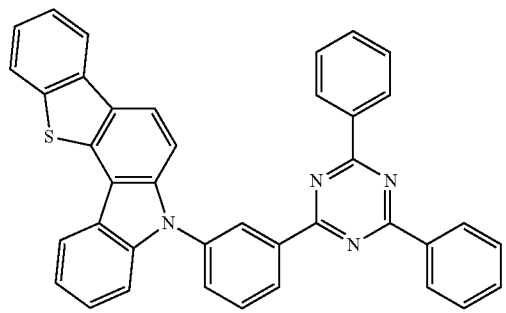
(EH-5)
(EH-6)
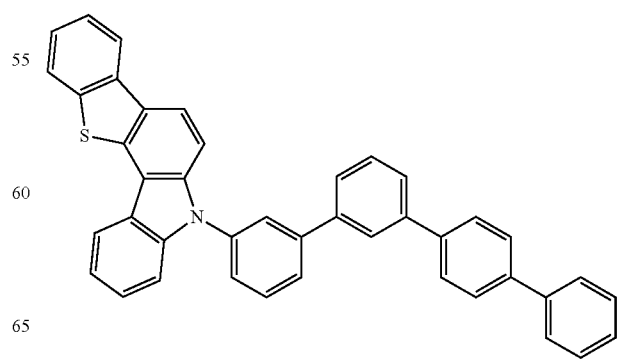

(EH-7)

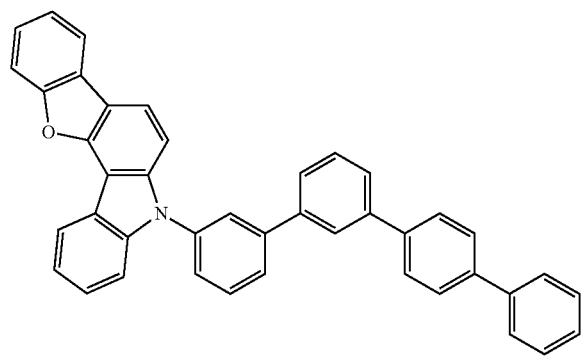

Example 1

<Fabrication and Evaluation of Organic Electroluminescent Elements>

The materials used for the fabrication of organic electroluminescent elements were all subjected to sublimation purification and it was confirmed that the purity (absorption intensity area ratio at 254 nm) was 99.9% or more by using high performance liquid chromatography (TSKgel ODS-100Z, manufactured by Tosoh Corporation).

The structures of the materials other than the light emitting materials used for the fabrication of the organic electroluminescent element in each of Examples and Comparative Examples are shown below.

[Chem. 35]

Comparative light emitting materials (Ir-1)

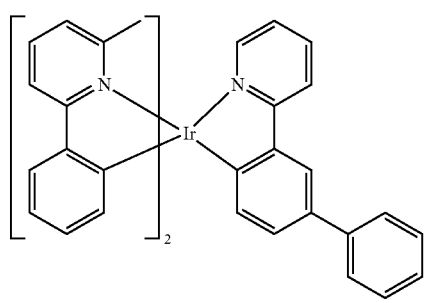

(Ir-2)

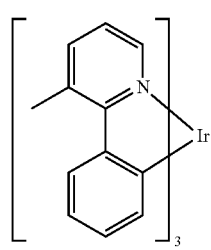

Comparative light emitting materials described in WO2009/148062 (EP2,301,921)

(Ir-3)

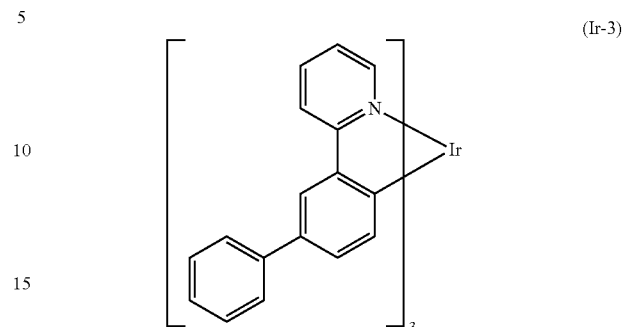

[Chem. 36]

Comparative host materials (RH-1)

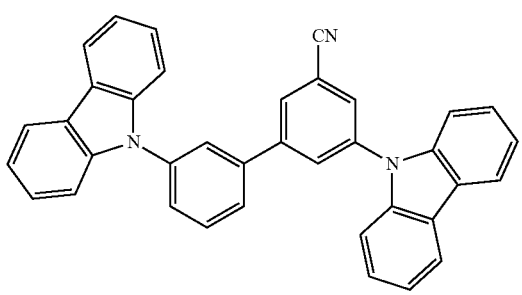

(RH-2)

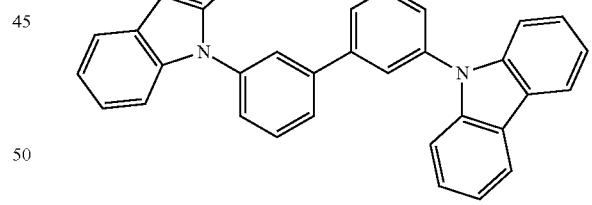

(RH-3)

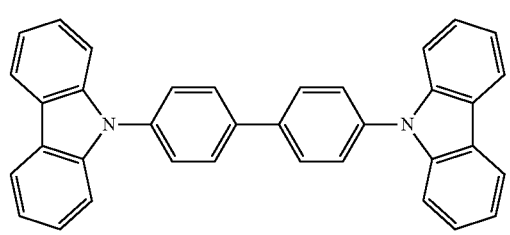

Comparative host materials described in WO2009/148062 (EP2,301,921)

(RH-4)

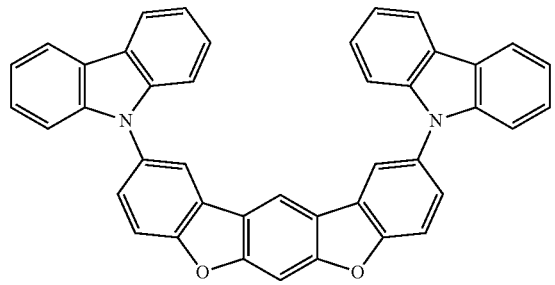

[Chem. 37]

Compound A (HAT-CN)

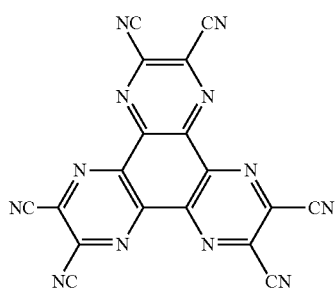

HTL-1

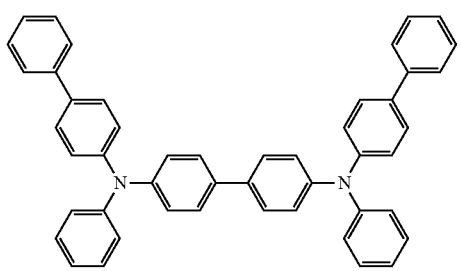

[Chem. 38]
Electron transporting materials

ETL-1 (OM-8)

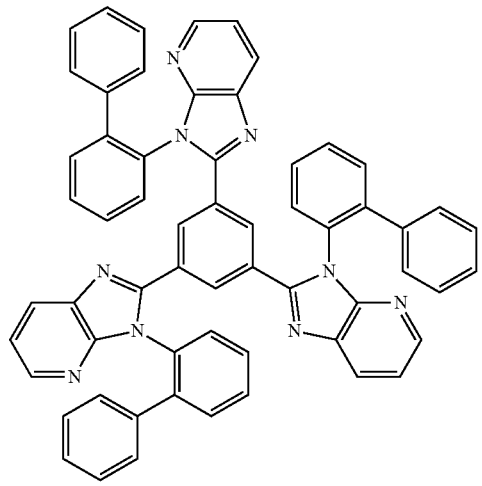

(ETL-2)

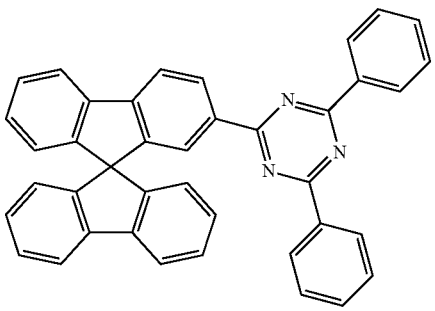

A 0.5 mm-thick and 2.5 cm square glass substrate (manufactured by Geomatec Co., Ltd., surface resistance: 10Ω/□) having an ITO film thereon was put in a cleaning container. After ultrasonic cleaning in 2-propanol, the glass substrate was subjected to a UV-ozone treatment for 30 minutes. The following organic layers were sequentially deposited on this transparent anode (ITO film) by a vacuum deposition method.

First layer (charge generating layer): Compound (A): film thickness of 10 nm

Second layer (hole transporting layer): HTL-1: film thickness of 30 nm

Third layer (light emitting layer): EH-1 (host compound) and light emitting material Pt-1 (the mass ratio of the host compound to the light emitting material is 85:15): film thickness of 40 nm Fourth layer: (electron transporting layer): ETL-1: film thickness of 40 nm 1 nm of lithium fluoride and 100 nm of metallic aluminum were deposited in this order thereon, thereby forming a cathode.

This laminate was put in a glove box purged with a nitrogen gas without bringing it into contact with the atmosphere and then sealed with a sealing can made of glass and an ultraviolet ray-curable adhesive (XNR5516HV, manufactured by Nagase-Chiba, Ltd.), thereby obtaining an organic electroluminescent element of Example 1.

Examples 2 to 17 and Comparative Examples 1 to 7

Organic electroluminescent elements of Example 2 to 17 and Comparative Example 1 to 7 were fabricated in the same manner as in Example 1, except that the light emitting material Pt-1 of the third layer was replaced by a compound shown in Table 1 below in the fabrication of the organic electroluminescent element of Example 1.

[Evaluation]

The organic electroluminescent element in each of Examples and Comparative Examples were evaluated by the following methods from the viewpoint of efficiency, durability, and driving voltage. The obtained results are shown in Table 1 below.

(Driving Voltage)

A direct current voltage was applied to the organic electroluminescent element in each of Examples and Comparative Examples to allow the element to emit light to give a luminance of 3500 cd/m$^2$. The voltage applied at this time was used as an index of the evaluation of the driving voltage. A case of the driving voltage being less than 6 V was rated as "B", a case of the driving voltage being 6 V or more and less than 8 V was rated as "C", and a case of the driving voltage being 8V or more was rated as "D", which are shown in Table 1 below.

less than 10 times, B denotes 3 times or more and less than 5 times, D denotes 1 time or more and less than 3 times, and DD denotes 0.1 times or more and less than 1 time.

TABLE 1

|  | Hole transporting layer | Light emitting material (light emitting layer) | Host compound (light emitting layer) | Electron transporting layer | Driving voltage | External quantum efficiency | Durability vs (Comparative Example 1) |
|---|---|---|---|---|---|---|---|
| Example 1 | HTL-1 | (Pt-1) | EH-1 | ETL-1 | B | B | BB |
| Example 2 | HTL-1 | (Pt-1) | EH-2 | ETL-1 | B | B | BB |
| Example 3 | HTL-1 | (Pt-1) | EH-3 | ETL-1 | B | A | BB |
| Example 4 | HTL-1 | (Pt-1) | EH-4 | ETL-1 | B | B | BB |
| Example 5 | HTL-1 | (Pt-1) | EH-5 | ETL-1 | B | A | BB |
| Example 6 | HTL-1 | (Pt-1) | EH-6 | ETL-1 | B | B | A |
| Example 7 | HTL-1 | (Pt-1) | EH-7 | ETL-1 | B | A | BB |
| Example 8 | HTL-1 | (Pt-2) | EH-6 | ETL-1 | B | A | A |
| Example 9 | HTL-1 | (Pt-3) | EH-6 | ETL-1 | B | A | A |
| Example 10 | HTL-1 | (Pt-2) | EH-7 | ETL-1 | B | A | A |
| Example 11 | HTL-1 | (Pt-3) | EH-7 | ETL-1 | B | A | A |
| Example 12 | HTL-1 | (Pt-4) | EH-7 | ETL-1 | B | A | BB |
| Example 13 | HTL-1 | (Pt-5) | EH-7 | ETL-1 | B | A | BB |
| Example 14 | HTL-1 | (Pt-6) | EH-7 | ETL-1 | B | B | BB |
| Example 15 | HTL-1 | (Pt-7) | EH-7 | ETL-1 | B | A | BB |
| Example 16 | HTL-1 | (Pt-8) | EH-7 | ETL-1 | B | A | BB |
| Example 17 | HTL-1 | (Pt-1) | EH-7 | ETL-2 | B | B | BB |
| Comparative Example 1 | HTL-1 | (Pt-1) | RH-1 | ETL-1 | B | D | D |
| Comparative Example 2 | HTL-1 | (Pt-1) | RH-2 | ETL-1 | D | B | DD |
| Comparative Example 3 | HTL-1 | (Pt-1) | RH-3 | ETL-1 | D | B | DD |
| Comparative Example 4 | HTL-1 | (Pt-1) | RH-3 | ETL-2 | D | D | DD |
| Comparative Example 5 | HTL-1 | (Ir-1) | EH-1 | ETL-1 | B | B | D |
| Comparative Example 6 | HTL-1 | (Ir-2) | EH-1 | ETL-1 | B | B | D |
| Comparative Example 7 | HTL-1 | (Ir-3) | RH-4 | ETL-1 | B | B | D |

(External Quantum Efficiency)

A direct current voltage was applied to the organic electroluminescent element in each of Examples and Comparative Examples by using a source measure unit 2400 manufactured by TOYO Corporation to allow the element to emit light, and the luminance was measured using a luminance meter BM-8 manufactured by Topcon Corporation. The luminous spectrum and the light emitting peak wavelength were measured using a spectrum analyzer PMA-11 manufactured by Hamamatsu Photonics K. K. Based on these values, the external quantum efficiency at a luminance in the vicinity of 3500 cd/m$^2$ was calculated by a luminance conversion method.

A case of the external quantum efficiency being 15% or more was rated as A, a case of the external quantum efficiency being 10% or more and less than 15% was rated as B, a case of the external quantum efficiency being 5% or more and less than 10% was rated as C, and a case of the external quantum efficiency being less than 5% was rated as D, which are shown in Table 1 below.

(Durability)

A direct current voltage was applied to the organic electroluminescent element in each of Examples and Comparative Examples to allow the element to emit light continuously to give a luminance of 3500 cd/m$^2$ at room temperature (20° C.). The time period required for the luminance to go down to 3395 cd/m$^2$ was used as an index of durability. The times of the time period of durability required for the luminance to go down to 3395 cd/m$^2$, relative to the time period of durability of the organic electroluminescent element of Comparative Example 1, in which the comparative compound (RH-1) was used as a host material, were calculated, and shown in Table 1 below.

Relative to the time period of durability of the organic electroluminescent element of Comparative Example 1, A denotes 10 times or more, BB denotes 5 times or more and From Table 1, it could be seen that by using the compound represented by the general formula (1) as a light emitting material and using a compound represented by the general formula (H-1) as a host material, an organic electroluminescent element having excellent luminous efficiency with a low driving voltage and excellent durability is obtained.

In the case of a light emitting device, a display device, and an illumination device, it is necessary to emit light at a high luminance instantly through a high current density in each of pixel portions, and accordingly, the light emitting element of the present invention can be advantageously used since it is designed to have high luminous efficiency in such a case.

In addition, the element of the present invention also has excellent durability, and is thus suitable for a light emitting device, a display device, and an illumination device.

REFERENCE SIGNS LIST

2: substrate
3: anode
4: hole injecting layer
5: hole transporting layer
6: light emitting layer
7: hole blocking layer
8: electron transporting layer
9: cathode
10: organic electroluminescent element (organic EL element)
11: organic layer
12: protective layer
14: adhesive layer
16: sealing enclosure
20: light emitting device
30: light scattering member
30A: light incident surface
30B: light output surface 31: transparent substrate
32: fine particles
40: illumination device

The invention claimed is:
1. An organic electroluminescent element comprising:
a substrate;
a pair of electrodes including an anode and a cathode, disposed on the substrate; and
at least one organic layer including a light emitting layer, disposed between the electrodes,
wherein the light emitting layer contains at least one kind of light emitting material represented by the following general formula (1) and at least one kind of host material represented by the following general formulae (H-2) or (H-5):

General Formula (1)

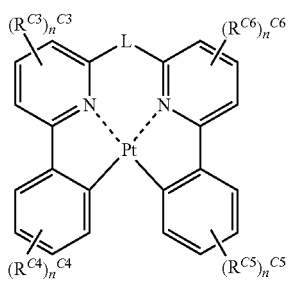

L represents O, $NR^{C0}$, or $CR^{C1}R^{C2}$;
$R^{C0}$ to $R^{C2}$ each independently represents a substituent selected from the group consisting of a $C_{1-10}$ alkyl group and a $C_{6-12}$ aryl group wherein two $C_{6-12}$ aryl groups may be bonded to form a fused ring;
$R^{C3}$ to $R^{C6}$ each independently represents a substituent selected from the group consisting of a $C_{1-10}$ alkyl group, a $C_{6-12}$ aryl group, and a cyano group;
$n^{C3}$ and $n^{C6}$ each independently represents an integer of 0 to 3, and $n^{C4}$ and $n^{C5}$ each independently represents an integer of 0 to 4; wherein when $n^{C3}$ to $n^{C6}$ are 2 or more, a plurality of $R^{C3}$s to $R^{C6}$s may be respectively the same as or different from each other:

General Formula (H-2)

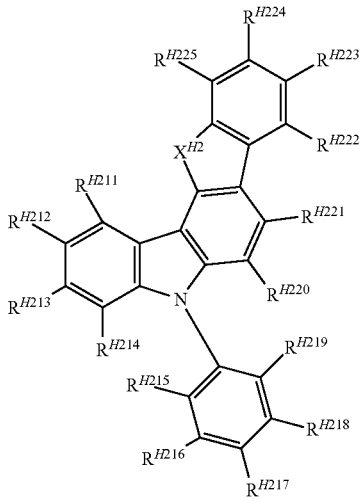

wherein $R^{H211}$ to $R^{H214}$, $R^{H220}$, $R^{H221}$, and $R^{H222}$ to $R^{H225}$ are each a hydrogen atom;
$R^{H215}$ to $R^{H219}$ is each independently selected from the group consisting of a hydrogen atom, a $C_{6-12}$ aryl group, a $C_{3-12}$ aromatic heterocyclic group, and combinations thereof;
$X^{H2}$ represents either of O and S:

General Formula (H-5)

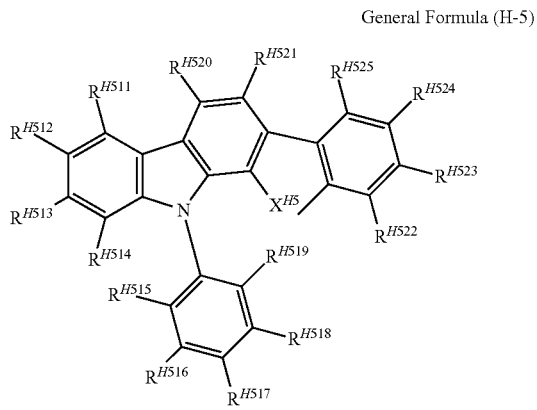

wherein $R^{H511}$ to $R^{H525}$ are each a hydrogen atom;
$X^{H5}$ represents $NR^{H526}$; and
$R^{H526}$ represents a substituent selected from the group consisting of a $C_{6-12}$ aryl group, a $C_{3-24}$ aromatic heterocyclic group, and combinations thereof.

2. The organic electroluminescent element according to claim 1, wherein the light emitting material represented by the general formula (1) is a light emitting material represented by the following general formula (11):

General Formula (11)

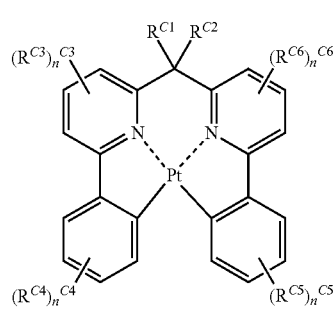

wherein $R^{C1}$ and $R^{C2}$ each independently represents a substituent selected from the group consisting of a $C_{1-10}$ alkyl group and a $C_{6-12}$ aryl group wherein two $C_{6-12}$ aryl groups may be bonded to form a ring; and
$R^{C3}$ to $R^{C6}$ each independently represents a substituent selected from the group consisting of a $C_{1-10}$ alkyl group, a $C_{6-12}$ aryl group, and a cyano group;
$n^{C3}$ and $n^{C6}$ each represents an integer of 0 to 3, and $n^{C4}$ and $n^{C5}$ each represents an integer of 0 to 4; wherein when $n^{C3}$ to $n^{C6}$ are 2 or more, a plurality of $R^{C3}$s to $R^{C6}$s may be the same as or different from each other.

3. A light emitting device using the organic electroluminescent element according to claim 1.

4. A display device using the organic electroluminescent element according to claim 1.

5. An illumination device using the organic electroluminescent element according to claim 1.

6. The organic electroluminescent element according to claim 1, wherein the light emitting material represented by general formula (1) is selected from the group consisting of:
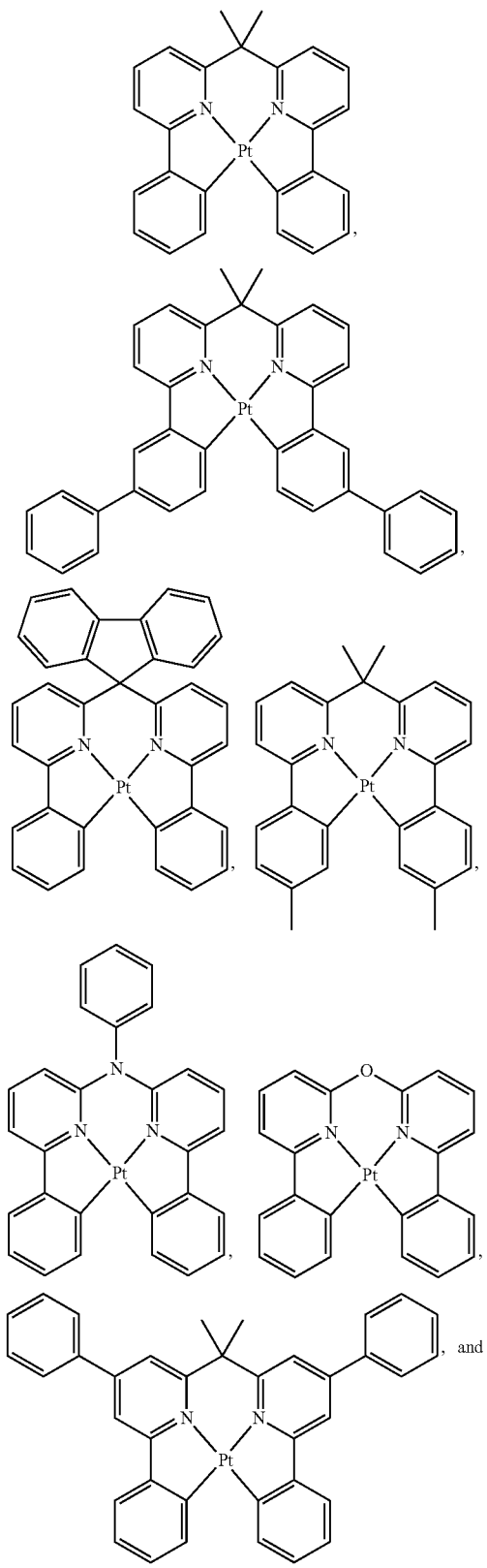
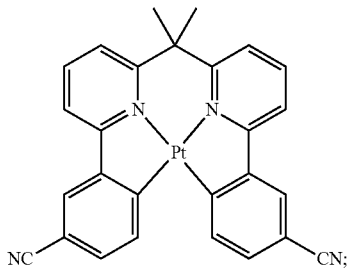
and wherein the host material represented by general formula (H-2) and (H-5) is selected from the group consisting of:
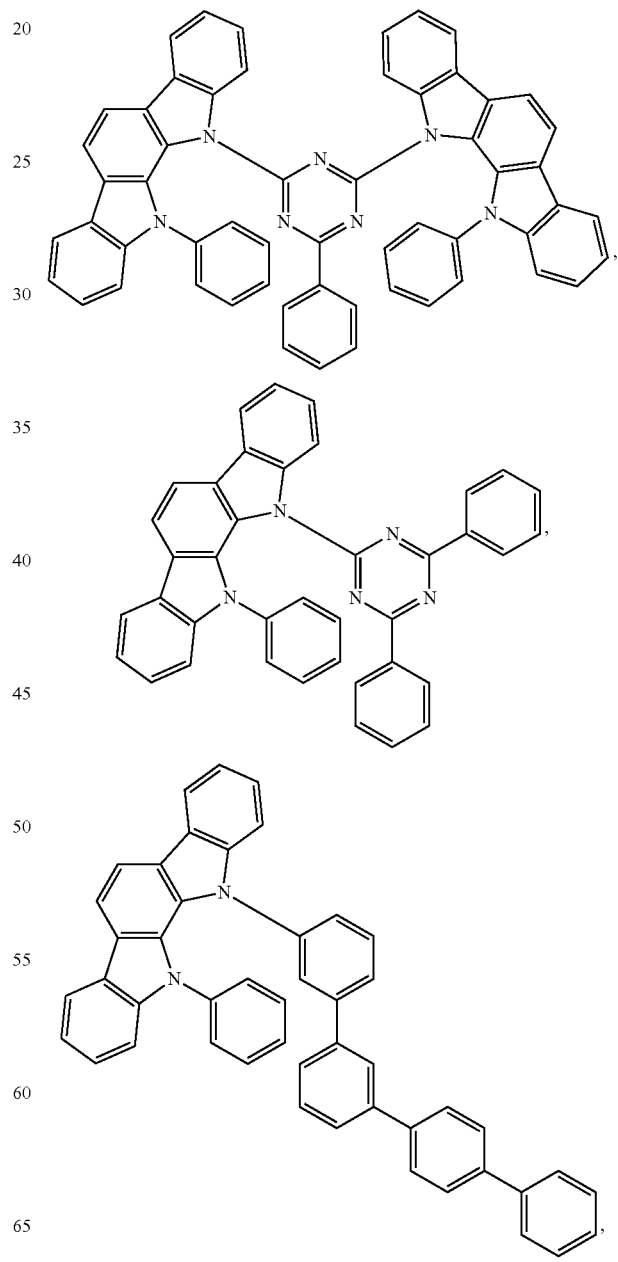

-continued

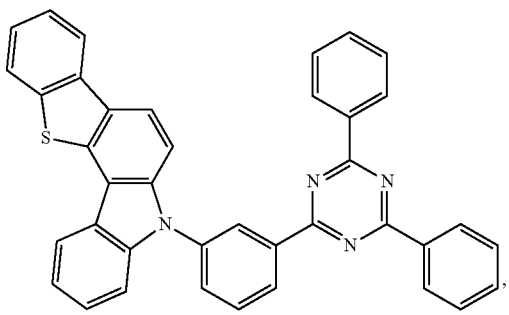,

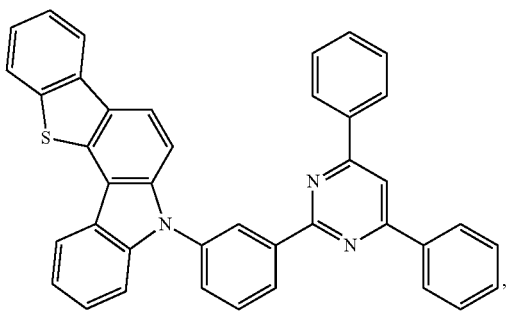,

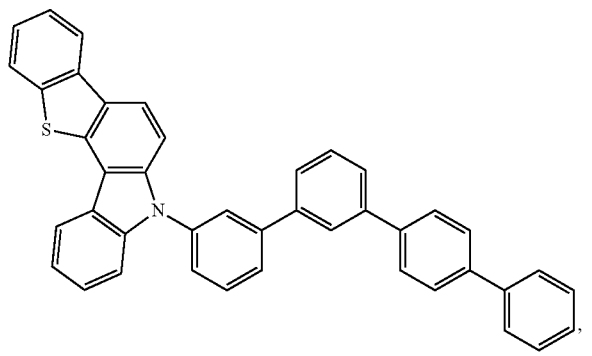, and

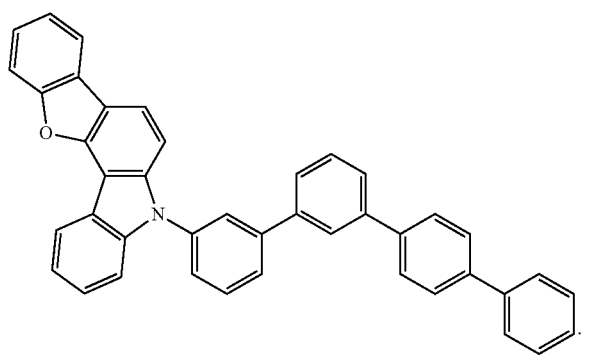.

7. A composition comprising a compound of general formula (1) and a compound of general formula (H-2) or general formula (H-5):

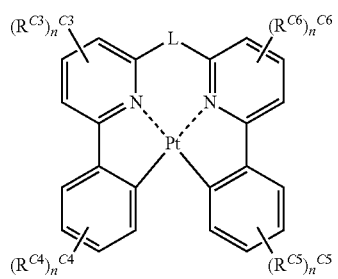

General Formula (1)

L represents O, $NR^{C0}$, or $CR^{C1}R^{C2}$;

$R^{C0}$ to $R^{C2}$ each independently represents a substituent selected from the group consisting of a $C_{1-10}$ alkyl group and a $C_{6-12}$ aryl group wherein two $C_{6-12}$ aryl groups may be bonded to form a fused ring;

$R^{C3}$ to $R^{C6}$ each independently represents a substituent selected from the group consisting of a $C_{1-10}$ alkyl group, a $C_{6-12}$ aryl group, and a cyano group;

$n^{C3}$ and $n^{C6}$ each independently represents an integer of 0 to 3, and $n^{C4}$ and $n^{C5}$ each independently represents an integer of 0 to 4; wherein when $n^{c3}$ to $n^{C6}$ are 2 or more, a plurality of $R^{C3}$s to $R^{C6}$s may be respectively the same as or different from each other:

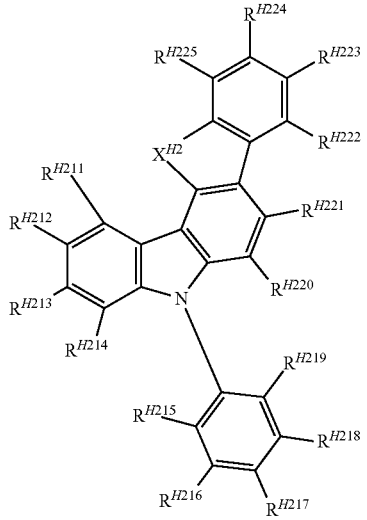

General Formula (H-2)

wherein $R^{H211}$ to $R^{H214}$, $R^{H220}$, $R^{H221}$, and $R^{H222}$ to $R^{H225}$ are each a hydrogen atom;

$R^{H215}$ to $R^{H219}$ is each independently selected from the group consisting of a hydrogen atom, a $C_{6-12}$ aryl group, a $C_{3-12}$ aromatic heterocyclic group, and combinations thereof;

$X^{H2}$ represents either of O and S:

General Formula (H-5)

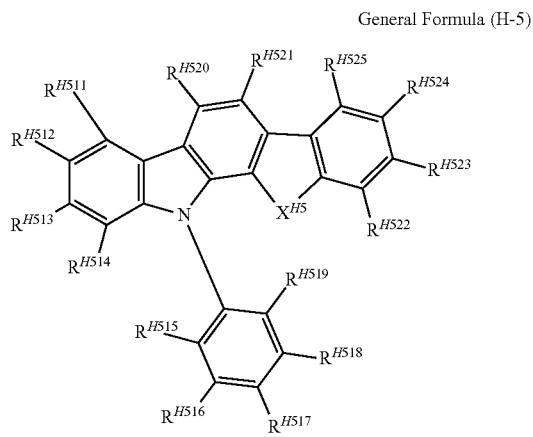

wherein $R^{H511}$ to $R^{H525}$ are each a hydrogen atom;
$X^{H5}$ represents $NR^{H526}$; and
$R^{H526}$ represents a substituent selected from the group consisting of a $C_{6-12}$ aryl group, a $C_{3-24}$ aromatic heterocyclic group, and combinations thereof.

8. The organic electroluminescent element according to claim 1, wherein
$R^{C0}$ to $R^{C2}$ each independently represents a substituent selected from the group consisting of a $C_{1-3}$ alkyl group and a phenyl ring, wherein two phenyl rings may be bonded to form a fused ring;
$R^{C3}$ to $R^{C6}$ each independently represents a substituent selected from the group consisting of a $C_{1-3}$ alkyl group, a phenyl ring, and a cyano group; and
$n^{C3}$, $n^{C4}$, $n^{C5}$, and $n^{C6}$ each independently represents an integer of 0 or 1.

9. The organic electroluminescent element according to claim 1, wherein
$R^{H215}$ to $R^{H219}$ is each independently selected from the group consisting of a hydrogen atom, a phenyl ring, a triazine ring, a pyrimidine ring, and combinations thereof.

10. The organic electroluminescent element according to claim 1, wherein
$R^{H526}$ represents a substituent selected from the group consisting of a phenyl ring, a triazine ring, a carbazole ring, a dibenzylamino group, and combinations thereof; and
the dibenzylamino group is optionally bonded to the carbazole ring to form a fused ring.

* * * * *